United States Patent
Suda

(10) Patent No.: US 9,761,811 B2
(45) Date of Patent: Sep. 12, 2017

(54) ORGANIC ELECTROLUMINESCENCE ELEMENT AND MATERIAL FOR ORGANIC ELECTROLUMINESCENCE ELEMENT

(71) Applicant: NIPPON STEEL & SUMIKIN CHEMICAL CO., LTD., Tokyo (JP)

(72) Inventor: Mitsuru Suda, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 371 days.

(21) Appl. No.: 14/404,255

(22) PCT Filed: May 15, 2013

(86) PCT No.: PCT/JP2013/063497
§ 371 (c)(1),
(2) Date: Nov. 26, 2014

(87) PCT Pub. No.: WO2014/002629
PCT Pub. Date: Jan. 3, 2014

(65) Prior Publication Data
US 2015/0188056 A1    Jul. 2, 2015

(30) Foreign Application Priority Data
Jun. 28, 2012    (JP) .................................. 2012-145210

(51) Int. Cl.
*H01L 51/00*    (2006.01)
*C07F 7/08*    (2006.01)
*H01L 51/50*    (2006.01)

(52) U.S. Cl.
CPC ........ *H01L 51/0069* (2013.01); *C07F 7/0816* (2013.01); *H01L 51/0067* (2013.01);
(Continued)

(58) Field of Classification Search
CPC ............... C07F 7/0816; H01L 51/0067; H01L 51/0069; H01L 51/0072; H01L 51/0073;
(Continued)

(56) References Cited

U.S. PATENT DOCUMENTS 8,927,749 B2 * 1/2015 Boudreault ......... H01L 51/0094
257/40
2002/0034655 A1    3/2002 Watanabe et al.
(Continued)

FOREIGN PATENT DOCUMENTS

JP    8-302339 A    11/1996
JP    2011-228615 A    11/2011
(Continued)

OTHER PUBLICATIONS

International Search Report for the Application No. PCT/JP2013/063497 mailed Aug. 6, 2013.
(Continued)

*Primary Examiner* — Dawn Garrett
(74) *Attorney, Agent, or Firm* — Cheng Law Group, PLLC

(57) ABSTRACT

Provided are a novel organic electroluminescent device material and an organic electroluminescent device using the same. The organic electroluminescent device material includes a compound represented by the following formula (1). The organic electroluminescent device of the present invention includes a substrate, an anode, an organic layer, and a cathode, the anode, the organic layer, and the cathode being laminated on the substrate, in which the organic layer contains the organic electroluminescent device material. The organic electroluminescent device material is suitable as a host material for a light-emitting layer containing a phosphorescent light-emitting dopant. In the formula, L represents an aromatic group including at least one aromatic
(Continued)

heterocyclic group, and $Ar_1$ to $Ar_4$ each represent an aromatic group.

9 Claims, 1 Drawing Sheet

(52) U.S. Cl.
CPC ...... *H01L 51/0072* (2013.01); *H01L 51/0073* (2013.01); *H01L 51/0094* (2013.01); *H01L 51/5016* (2013.01); *H01L 51/5056* (2013.01); *H01L 51/5072* (2013.01); *H01L 51/5096* (2013.01)

(58) Field of Classification Search
CPC ............. H01L 51/0094; H01L 51/5016; H01L 51/5056; H01L 51/5072; H01L 51/5096
See application file for complete search history.

(56) References Cited

U.S. PATENT DOCUMENTS

| | | | |
|---|---|---|---|
| 2004/0124766 A1* | 7/2004 | Nakagawa | H01L 51/0064 313/504 |
| 2009/0273278 A1 | 11/2009 | Lee et al. | |
| 2010/0051106 A1 | 3/2010 | Kim et al. | |
| 2010/0096982 A1 | 4/2010 | Eum et al. | |
| 2014/0158859 A1 | 6/2014 | Fukuzaki et al. | |

FOREIGN PATENT DOCUMENTS

| | | |
|---|---|---|
| WO | WO-01/41512 A1 | 6/2001 |
| WO | WO-2006/041263 A1 | 4/2006 |
| WO | WO 2011/136482 A1 * | 11/2011 |
| WO | WO-2011/136484 A1 | 11/2011 |
| WO | WO-2012/007103 A1 | 1/2012 |

OTHER PUBLICATIONS

Written Opinion of the International Searching Authority (PCT/ISA/237) for Application No. PCT/JP2013/063497 mailed Aug. 6, 2013 (English Translation).
Holmes, R. J. et al., "Blue organic electrophosphorescence using exothermic host-guest energy transfer", Applied Physics Letters, 2003, vol. 82, No. 15, pp. 2422-2424.
Tokito, Shizuo et al., "Confinement of triplet energy on phosphorescent molecules for highly-efficient organic blue-light-emitting devices", Applied Physics Letters, 2003, vol. 83, No. 3, pp. 569-571.

* cited by examiner

ORGANIC ELECTROLUMINESCENCE ELEMENT AND MATERIAL FOR ORGANIC ELECTROLUMINESCENCE ELEMENT

TECHNICAL FIELD

The present invention relates to an organic electroluminescent device material and an organic electroluminescent device using the same, and more specifically, to a thin-film-type device that emits light when an electric field is applied to a light-emitting layer formed of an organic compound.

BACKGROUND ART

In general, an organic electroluminescent device (hereinafter referred to as organic EL device) includes a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine and a light-emitting layer formed of an 8-hydroxyquinoline aluminum complex (hereinafter referred to as Alq3) are formed between electrodes as thin films, resulting in a significant improvement in luminous efficiency, as compared to related-art devices in which a single crystal of anthracene or the like is used. Thus, the development of the above-mentioned organic EL device has been promoted in order to accomplish its practical application to a high-performance flat panel having features such as self-luminescence and rapid response.

Further, studies have been made on using phosphorescent light rather than fluorescent light as an attempt to raise the luminous efficiency of a device. Many kinds of devices including the above-mentioned device in which a hole-transporting layer formed of an aromatic diamine and a light-emitting layer formed of Alq3 are formed emit light by using fluorescent light emission. However, by using phosphorescent light emission, that is, by using light emission from a triplet excited state, luminous efficiency is expected to be improved by from about three times to four times, as compared to the case of using related-art devices in which fluorescent light (singlet) is used. In order to accomplish this purpose, studies have been made on adopting a coumarin derivative or a benzophenone derivative as a light-emitting layer, but extremely low luminance has only been provided. Further, studies have been made on using a europium complex as an attempt to use a triplet state, but highly efficient light emission has not been accomplished. In recent years, many studies centered on an organic metal complex such as an iridium complex have been made, as described in Patent Literature 1, for the purpose of attaining the high efficiency and long lifetime of light emission.

In order to obtain high luminous efficiency, host materials that are used with the dopant materials described above play an important role. A typical example of the host materials proposed is 4,4'-bis(9-carbazolyl)biphenyl (hereinafter referred to as CBP) as a carbazole compound disclosed in Patent Literature 2. When CBP is used as a host material for a green phosphorescent light-emitting material typified by a tris(2-phenylpyridine)iridium complex (hereinafter referred to as Ir(ppy)3), a relatively satisfactory light-emitting characteristic is exhibited. Meanwhile, when CBP is used as a host material for a blue phosphorescent light-emitting material, sufficient luminous efficiency is not obtained. This is because an energy level in the lowest excited triplet state of CBP is lower than that of a general blue phosphorescent light-emitting material, and hence triplet excitation energy of the blue phosphorescent light-emitting material transfers to CBP. That is, when the phosphorescent host material has higher triplet excitation energy than the phosphorescent light-emitting material, the triplet excitation energy of the phosphorescent light-emitting material is effectively confined, and as a result, high luminous efficiency is achieved. With the purpose of improving the energy confinement effect, in Non Patent Literature 1, the triplet excitation energy is increased by modification of structure of CBP, to thereby improve luminous efficiency of a bis[2-(4,6-difluorophenyl)pyridinato-N,C2'](picolinato)iridium complex (hereinafter referred to as FIrpic). In addition, in Non Patent Literature 2, 1,3-dicarbazolylbenzene (hereinafter referred to as mCP) is used as a host material to improve luminous efficiency on the basis of a similar effect. However, those materials are not satisfactory for practical use particularly from the viewpoint of durability.

In order to obtain high luminous efficiency, there are also needed balanced injecting/transporting characteristics for both charges (a hole and an electron). CBP is poorer in electron-transporting ability than in hole-transporting ability, and hence the balance between charges in the light-emitting layer is disturbed. As a result, excessive holes flow out to the cathode side to reduce a recombination probability in the light-emitting layer, resulting in a reduction in luminous efficiency. Further, in this case, a recombination region in the light-emitting layer is limited to a small region in the vicinity of an interface on the cathode side. Accordingly, when an electron-transporting material, such as Alq3, having a lower energy level in the lowest excited triplet state than Ir(ppy)3 is used, there may occur a reduction in luminous efficiency due to transfer of the triplet excitation energy from the dopant to the electron-transporting material.

As described above, in order to obtain high luminous efficiency in an organic EL device, there is needed a host material that has high triplet excitation energy and balanced injecting/transporting characteristics for both charges (a hole and an electron). Further desired is a compound that is electrochemically stable, has high heat resistance, and has excellent amorphous stability, and hence a further improvement has been demanded.

In addition, as an organic EL device using a cyclic compound containing Si in its ring, in Patent Literature 3, there is disclosed an organic EL device using the following compound (a1) as a hole-transporting layer material.

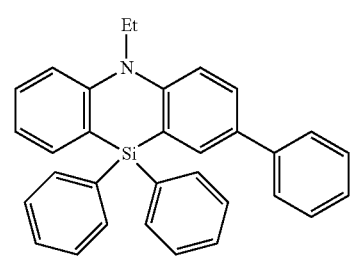

(a1)

In addition, as an organic EL device using a cyclic compound containing Si in its ring, in Patent Literature 4, there is disclosed an organic EL device using the following compound (a2) or (a3) as a hole-transporting material. In the formulae, $X_{10}$, $X_{11}$, $X_{16}$, and $X_{17}$ each represent $CR_2$, O, S, NR, $SiR_2$, or $GeR_2$, and $R_8$ represents a substituted or unsubstituted alkylene group or a divalent aromatic hydrocarbon group. However, the compound (a2) means a trimer, and the compound (a3) means a dimer linked through a hydrocarbon group.

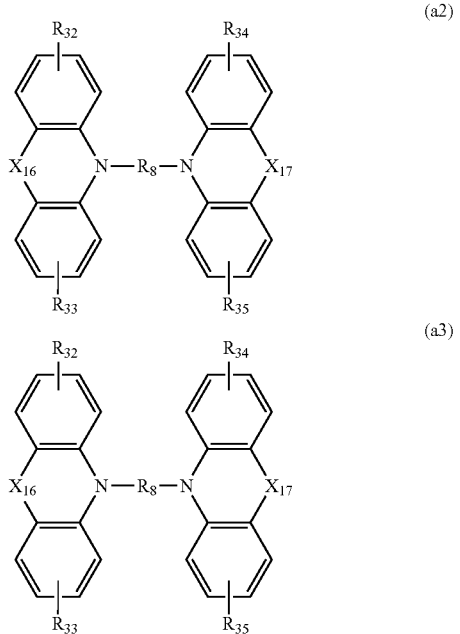

CITATION LIST

Patent Literature

[PTL 1] WO 01/041512 A1
[PTL 2] JP 2001-313178 A
[PTL 3] JP 8-302339 A
[PTL 4] WO 2006/041263 A1

Non Patent Literature

[NPL 1] Applied Physics Letters, 2003, 83, 569-571.
[NPL 2] Applied Physics Letters, 2003, 82, 2422-2424.

SUMMARY OF INVENTION

Technical Problem

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, an organic EL device that has high efficiency, has high driving stability, and is practically useful, and a compound suitable for the organic EL device.

Solution to Problem

The inventor of the present invention has made extensive studies, and as a result, has found that a novel compound in which Si-containing rings are linked through an aromatic heterocyclic substituent has excellent characteristics as an organic electroluminescent device material. The inventor has also found that the use of the compound in an organic electroluminescent device allows the device to express excellent characteristics such as high efficiency and a long lifetime. Thus, the inventor has completed the present invention.

The present invention relates to an organic electroluminescent device material, including a compound represented by the general formula (1).

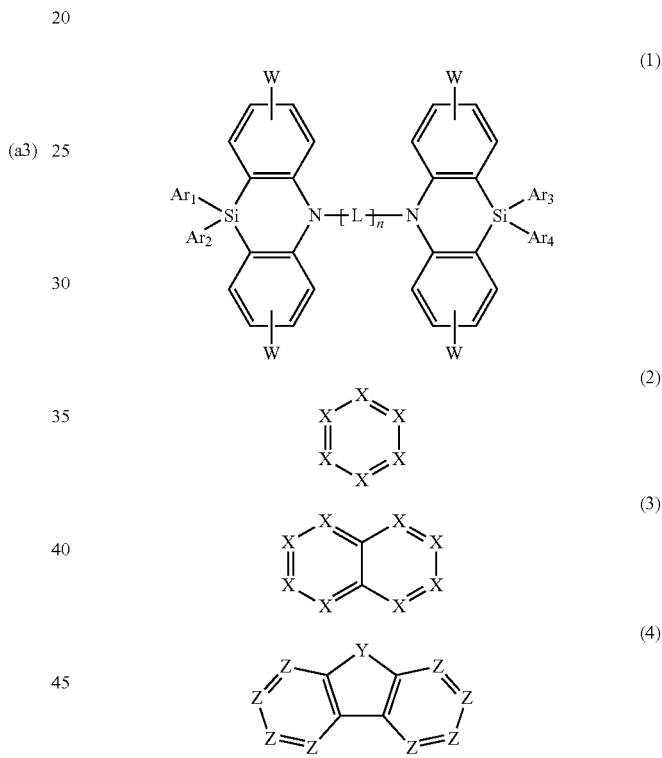

In the general formula (1):

L represents a divalent aromatic group selected from an aromatic hydrocarbon group having 6 to 50 carbon atoms and an aromatic heterocyclic group having 3 to 50 carbon atoms, the divalent aromatic group being represented by the formula (2), (3), or (4), and n represents an integer of from 1 to 6. When n represents 1, L represents the aromatic heterocyclic group, and when n represents 2 or more, at least one L represents the aromatic heterocyclic group. In each of the formula (2) and the formula (3), X's each independently represent methine, substituted methine, a carbon atom, or nitrogen, provided that any two of X's each represent a carbon atom to provide a divalent group. In the formula (4), Y represents NR, oxygen, or sulfur, R represents an aromatic hydrocarbon group having 6 to 50 carbon atoms or an aromatic heterocyclic group having 3 to 50 carbon atoms, and Z's each independently represent methine, substituted methine, a carbon atom, or nitrogen, provided that any two of Z's each represent a carbon atom to provide a divalent group. Substituents in a case where X's or Z's represent substituted methine each independently represent an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 50 carbon atoms, or an aromatic heterocyclic group having 3 to 50 carbon atoms. W's each independently represent the same substituent as in the case of substituted methine, or hydrogen. $Ar_1$ to $Ar_4$ each independently represent an aromatic hydrocarbon group having 6 to 50 carbon atoms or an aromatic heterocyclic group having 3 to 50 carbon atoms.

In the general formula (1), it is preferred that L represent a divalent aromatic group represented by the formula (2) or (4). In addition, it is preferred that at least one of X's in the formula (2) represent nitrogen, and it is preferred that six of Z's in the formula (4) each represent methine and two of Z's in the formula (4) each represent a carbon atom.

It is preferred that the compound represented by the general formula (1) include a compound represented by the general formula (5).

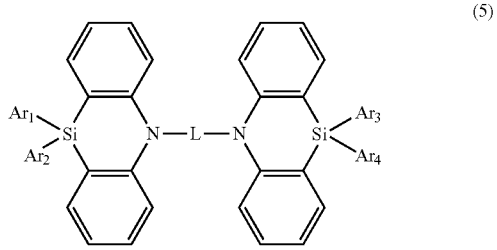

(5)

In the general formula (5), L and $Ar_1$ to $Ar_4$ have the same meanings as in the general formula (1). It is preferred that $Ar_1$ to $Ar_4$ each represent a phenyl group. It should be noted that L in the general formula (5) is limited to a divalent aromatic heterocyclic group.

In addition, another aspect of the present invention relates to an organic electroluminescent device, including: a substrate; an anode; at least one organic layer; and a cathode, the anode, the at least one organic layer, and the cathode being laminated on the substrate, in which the at least one organic layer includes an organic layer containing the organic electroluminescent device material including the compound represented by the general formula (1).

It is preferred that the organic layer containing the organic electroluminescent device material include at least one layer selected from the group consisting of a light-emitting layer, an electron-transporting layer, a hole-transporting layer, an electron-blocking layer, and a hole-blocking layer. It is more preferred that the organic layer containing the organic electroluminescent device material include a light-emitting layer containing a phosphorescent light-emitting dopant.

Effects of Invention

The compound represented by the general formula (1) linked through an aromatic heterocyclic group (hereinafter sometimes referred to as compound of the present invention), which serves as the organic electroluminescent device material of the present invention, is improved in electron-transporting property by virtue of the aromatic heterocyclic group having high electron-transporting property, which is linked to the unit having high hole-transporting property.

Consequently, the compound provides a satisfactory balance among various energy values, i.e., ionization potential, electron affinity, and triplet excitation energy. Further, it is considered that the compound is allowed to have a high charge-resisting characteristic and a satisfactory charge balance by virtue of the presence of the HOMO in the unit having high hole-transporting property, and the presence of the LUMO in the aromatic heterocyclic group having high electron-transporting property.

DESCRIPTION OF EMBODIMENTS

Figure 1:
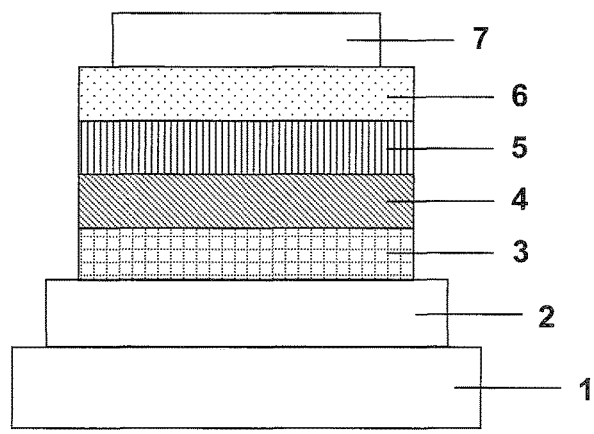
FIG. 1 is a schematic sectional view illustrating a structural example of an organic EL device.

An organic electroluminescent device material of the present invention includes a compound represented by the general formula (1).

In the general formula (1), L represents a divalent aromatic group represented by the formula (2), (3), or (4), preferably the formula (2) or (4). The divalent aromatic group is an aromatic hydrocarbon group having 6 to 50 carbon atoms or an aromatic heterocyclic group having 3 to 50 carbon atoms, provided that at least one of n L's represents an aromatic heterocyclic group. n represents an integer of from 1 to 6, preferably from 1 to 3, more preferably 1.

W's each independently represent hydrogen, an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 50 carbon atoms, or an aromatic heterocyclic group having 3 to 50 carbon atoms.

$Ar_1$ to $Ar_4$ each independently represent an aromatic hydrocarbon group having 6 to 50 carbon atoms or an aromatic heterocyclic group having 3 to 50 carbon atoms.

In the formula (2) and the formula (3), X's each independently represent methine, substituted methine, a carbon atom, or nitrogen.

In the formula (4), Y represents NR, oxygen, or sulfur, R represents an aromatic hydrocarbon group having 6 to 50 carbon atoms or an aromatic heterocyclic group having 3 to 50 carbon atoms, and Z's each independently represent methine, substituted methine, a carbon atom, or nitrogen.

L represents a divalent group, and hence two X's or two Z's in each of the formulae (2) to (4) represent carbon atoms to provide the divalent group.

When any X or Z represents substituted methine, its substituent is the same as any one of the groups given in the foregoing description of W's (excluding hydrogen).

In the formula (2), it is preferred that two of six X's each represent C, zero to three thereof each represent N, and one to four thereof each represent methine or substituted methine, and it is more preferred that at least one thereof represent N. In the formula (3), it is preferred that two of eight X's each represent C, zero to four thereof each represent N, and two to six thereof each represent methine or substituted methine, and it is more preferred that at least one thereof represent N. In the formula (4), it is preferred that two of eight Z's each represent C, zero to four thereof each represent N, and two to six thereof each represent methine or substituted methine, and it is more preferred that six thereof each represent methine.

When L represents an aromatic heterocyclic group, in the formula (2), it is preferred that two of six X's each represent C, one to three thereof each represent N, and one to three thereof each represent methine or substituted methine, and in the formula (3), it is preferred that two of eight X's each represent C, one to four thereof each represent N, and two to five thereof each represent methine or substituted methine.

In addition, when X's or Z's in the formula each represent methine or substituted methine, it is preferred that the number of X's or Z's each representing methine be larger than the number of X's or Z's each representing substituted methine. It is more preferred that the number of X's or Z's each representing substituted methine be 0 or 1.

When L represents a divalent unsubstituted aromatic group, specific examples of the divalent unsubstituted aromatic group include: aromatic hydrocarbon groups produced by removing two hydrogen atoms from benzene and naphthalene; and aromatic heterocyclic groups produced by removing two hydrogen atoms from dibenzofuran, dibenzothiophene, pyridine, pyrazine, pyrimidine, pyridazine, triazine, isoquinoline, carbazole, naphthyridine, phthalazine, quinazoline, quinoxaline, cinnoline, quinoline, and pteridine. Preferred examples thereof include: aromatic hydrocarbon groups produced by removing two hydrogen atoms from benzene and naphthalene; and aromatic heterocyclic groups produced by removing two hydrogen atoms from dibenzofuran, dibenzothiophene, pyridine, pyrazine, pyrimidine, pyridazine, triazine, and carbazole. More preferred examples thereof include aromatic heterocyclic groups produced by removing two hydrogen atoms from dibenzofuran, dibenzothiophene, pyridine, triazine, and carbazole. The divalent unsubstituted aromatic group is desirably a monocyclic aromatic group or an aromatic group in which two or three rings are fused.

The cases where L represents a divalent unsubstituted aromatic group include the case where X's each represent methine or nitrogen in the formula (2) or (3), and the case where Z's each represent methine or nitrogen and Y represents oxygen or sulfur in the formula (4). The cases where L represents an aromatic heterocyclic group include the case where at least one of X's represents nitrogen in the formula (2) or (3), and the case of the formula (4).

When n represents 1, L represents a divalent aromatic heterocyclic group. The case where n represents 1 and W's each represent H in the general formula (1) is represented by the general formula (5). In the general formula (5), L and $Ar_1$ to $Ar_4$ have the same meanings as in the general formula (1), but L is limited to the aromatic heterocyclic group. In addition, the case where $Ar_1$ to $Ar_4$ each represent phenyl in the general formula (5) is represented by the general formula (6). Any such compound is one of the preferred compounds.

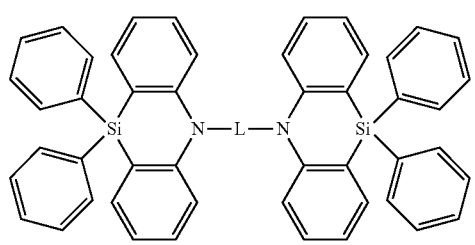

(6)

When n represents 2 or more, n L's are linked. The aromatic groups to be linked may be identical to or different from each other, and linking positions at which the aromatic groups are bonded are not limited. At least one of L's represents an aromatic heterocyclic group.

Specific examples of the unsubstituted aromatic group produced by linking n L's include divalent groups produced by removing two hydrogen atoms from bipyridine, bipyrimidine, bitriazine, terpyridine, bistriazylbenzene, biscarbazolylbenzene, carbazolylbiphenyl, biscarbazolylbiphenyl, carbazolylterphenyl, phenylpyridine, phenylcarbazole, diphenylcarbazole, diphenylpyridine, phenylpyrimidine, diphenylpyrimidine, phenyltriazine, diphenyltriazine, phenyldibenzofuran, phenyldibenzothiophene, diphenyldibenzofuran, diphenyldibenzothiophene, bidibenzofuran, bidibenzothiophene, bisdibenzofuranylbenzene, and bisdibenzothiophenylbenzene.

The aromatic group serving as L may have a substituent, which corresponds to the case where any X or Z represents substituted methine or Y represents NR in the general formula (2), (3), or (4).

In the general formula (2), (3), or (4), when any X or Z represents substituted methine, its substituent represents an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 50 carbon atoms, or an aromatic heterocyclic group having 3 to 50 carbon atoms, preferably an alkyl group having 1 to 10 carbon atoms, a cycloalkyl group having 3 to 10 carbon atoms, an alkenyl group having 2 to 10 carbon atoms, an alkynyl group having 2 to 10 carbon atoms, an aromatic hydrocarbon group having 6 to 24, more preferably 6 to 12 carbon atoms, or an aromatic heterocyclic group having 3 to 19, more preferably 3 to 10 carbon atoms. The aromatic hydrocarbon group or the aromatic heterocyclic group may be a monocyclic ring, or may be a fused ring, and is preferably a monocyclic ring or fused ring containing one to three rings.

Specific examples of the alkyl group include a methyl group, an ethyl group, a propyl group, a butyl group, a pentyl group, a hexyl group, a heptyl group, an octyl group, a nonyl group, and a decyl group. Preferred examples thereof include a methyl group, an ethyl group, a propyl group, a butyl group, a pentyl group, a hexyl group, a heptyl group, and an octyl group. The alkyl group may be linear or branched.

Specific examples of the cycloalkyl group include a cyclopropyl group, a cyclobutyl group, a cyclopentyl group, a cyclohexyl group, a cycloheptyl group, a cyclooctyl group, and a decahydronaphthyl group. A preferred example thereof is a cyclohexyl group.

Specific examples of the alkenyl group and the alkynyl group include an ethylenyl group, a propylenyl group, a butenyl group, a pentenyl group, a hexenyl group, a heptenyl group, an octenyl group, an acetylenyl group, a propynyl group, a butynyl group, and a pentynyl group. Preferred examples thereof include an ethylenyl group, a propylenyl group, a butenyl group, an acetylenyl group, and a propynyl group. The alkenyl group and the alkynyl group may be linear or branched.

Specific examples of the aromatic hydrocarbon group or the aromatic heterocyclic group include monovalent groups produced by removing one hydrogen atom from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, benzofuran, isobenzofuran, xanthene, oxathrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, benzisothiazole, and an aromatic compound in which a plurality of such aromatic rings are linked. Preferred examples thereof include monovalent groups produced by removing one hydrogen atom from benzene, naphthalene, phenanthrene, anthracene, triphenylene, pyrene, tetraphene, tetracene, perylene, pentaphene, pentacene, furan, benzofuran, xanthene, dibenzofuran, thiophene, thioxanthene, thianthrene, thionaphthene, dibenzothiophene, pyrrole, pyrazole, thiazole, oxazole, pyridine, pyrazine, pyrimidine, pyridazine, triazine, indole, carbazole, imidazole, naphthyridine, quinoline, phenanthroline, carboline, benzothiazole, benzimidazole, benzoxazole, and an aromatic compound in which a plurality of such aromatic rings are linked.

In addition, it is preferred that the aromatic heterocyclic group have 1 to 3 nitrogen, oxygen, or sulfur atoms in its ring. When a plurality of aromatic hydrocarbon groups or aromatic heterocyclic groups are linked, the number of aromatic rings to be linked is preferably from 1 to 5, more preferably from 1 to 3.

In addition, the aromatic hydrocarbon group or the aromatic heterocyclic group may have a substituent, and the substituent is preferably an alkyl group having 1 to 6 carbon atoms.

In the formula (4), R in the case where Y represents NR represents an aromatic hydrocarbon group having 6 to 50 carbon atoms or an aromatic heterocyclic group having 3 to 50 carbon atoms, preferably an aromatic hydrocarbon group having 6 to 24 carbon atoms or an aromatic heterocyclic group having 3 to 19 carbon atoms. Specific examples of the aromatic hydrocarbon group or the aromatic heterocyclic group are the same as those described for the substituent of the substituted methine.

In the general formula (1), W's each independently represent hydrogen or a group such as an alkyl group. The group such as the alkyl group, and specific examples thereof are the same as those described for the substituent of the substituted methine. W's each preferably represent hydrogen.

In the general formula (1), $Ar_1$ to $Ar_4$ each independently represent an aromatic hydrocarbon group having 6 to 50 carbon atoms or an aromatic heterocyclic group having 3 to 50 carbon atoms, preferably an aromatic hydrocarbon group having 6 to 24, more preferably 6 to 12 carbon atoms or an aromatic heterocyclic group having 3 to 19, more preferably 3 to 10 carbon atoms, still more preferably a phenyl group. Specific examples of the aromatic hydrocarbon group or the aromatic heterocyclic group are the same as those described for the substituent of the substituted methine.

Specific examples of the compound of the present invention represented by the general formula (1) are shown below, but the compound of the present invention is not limited thereto.

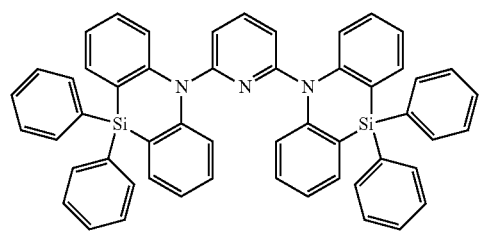
(1-1)

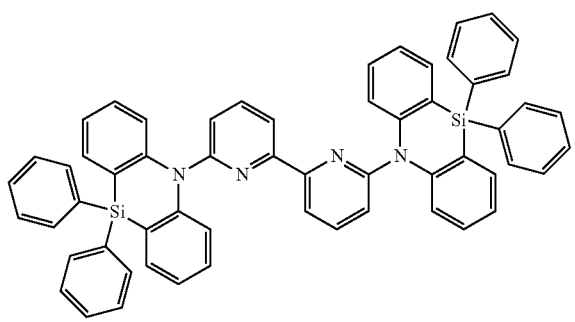
(1-2)

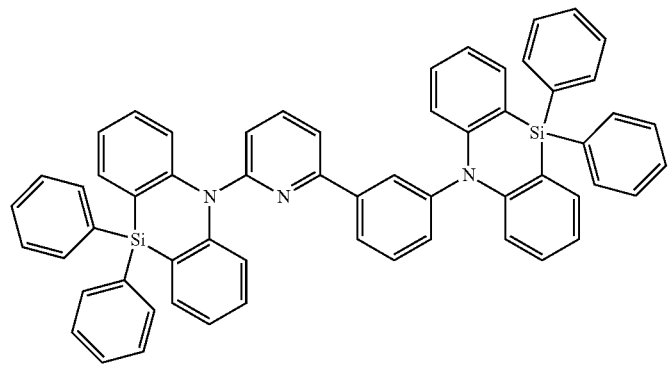
(1-3)

-continued
(1-4)
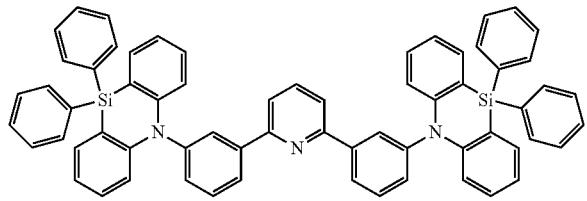
(1-5)
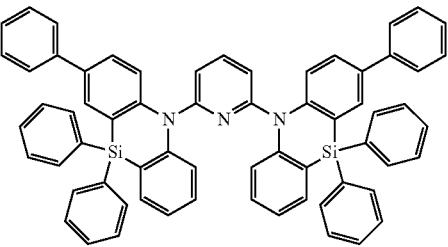
(1-6)
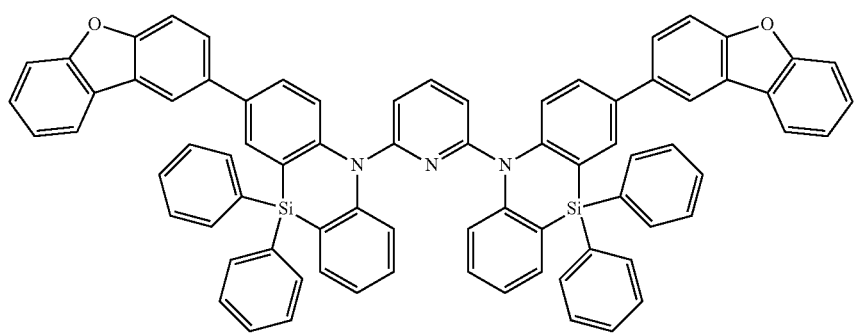
(1-7)
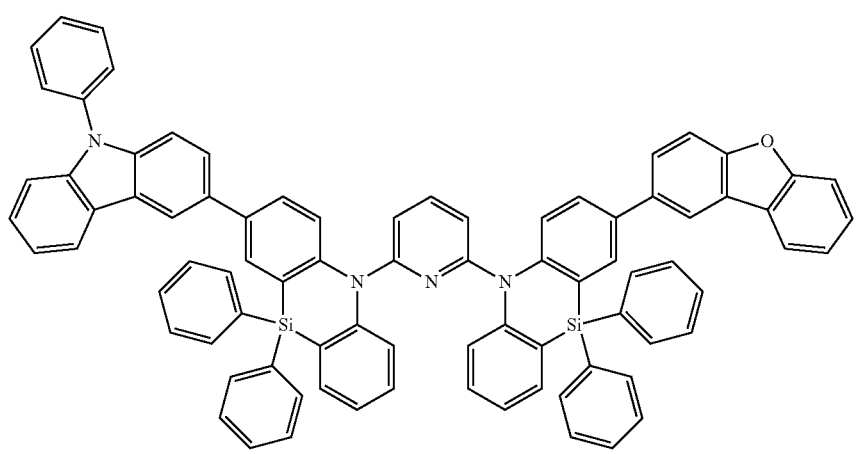
(1-8)
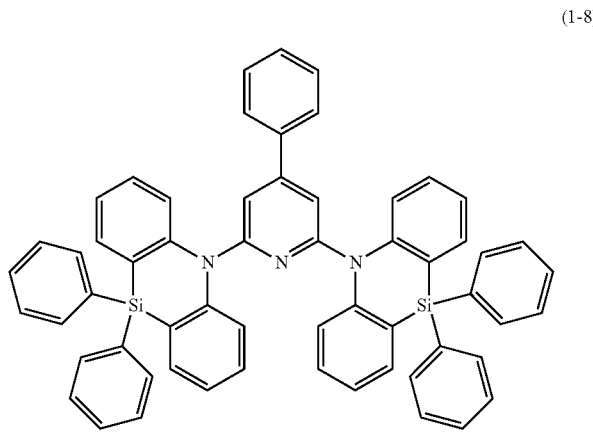
(1-9)
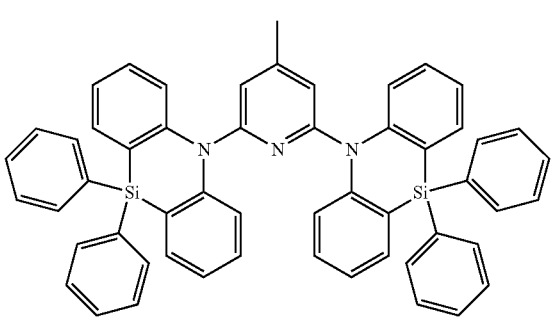

-continued
(1-10)
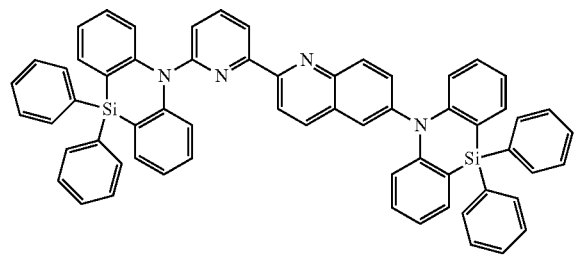
(1-11)
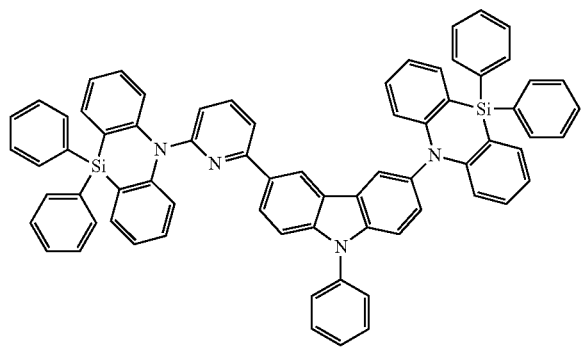
(1-12)
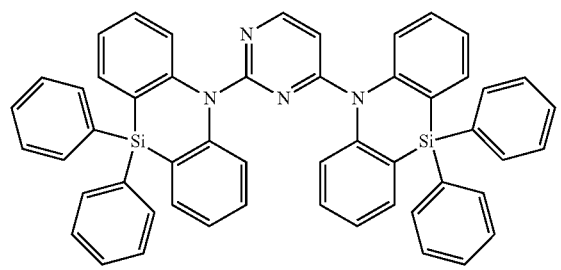
(1-13)
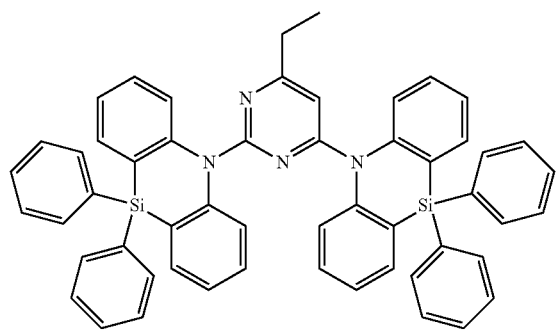
(1-14)
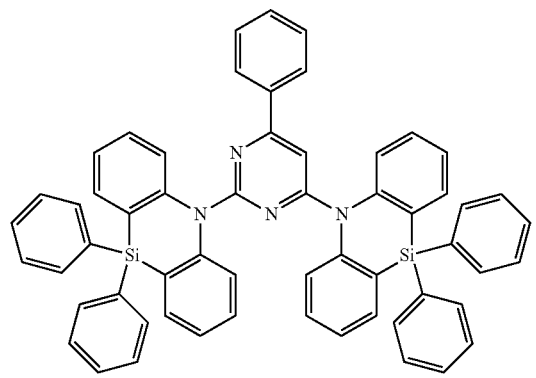
(1-15)
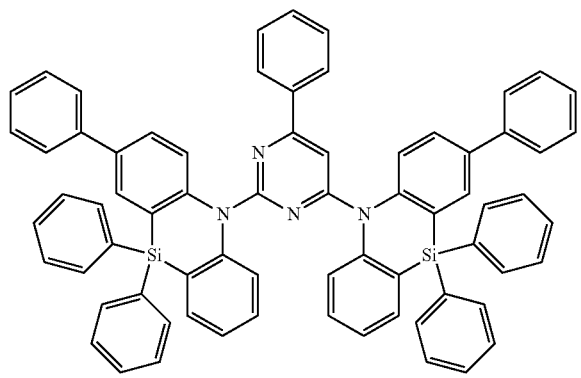
(1-16)
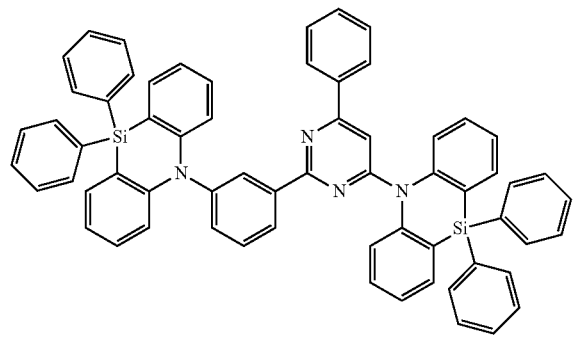
(1-17)
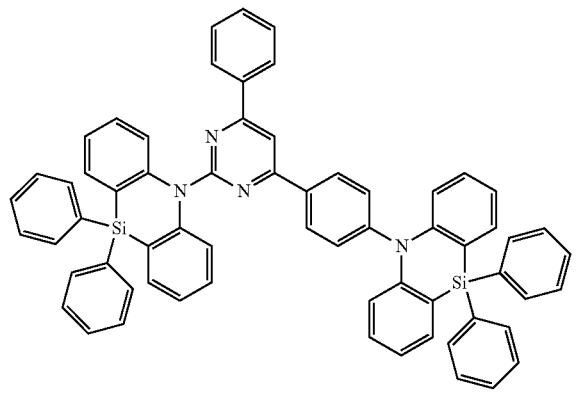

-continued
(1-18)
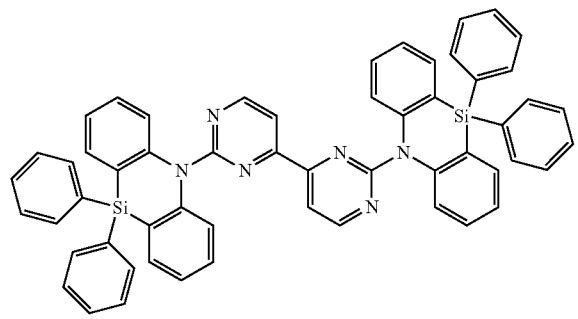
(1-19)
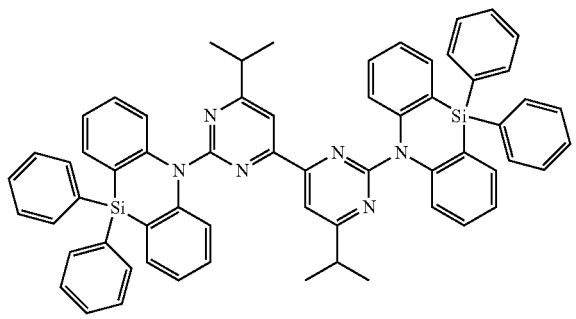
(1-20)
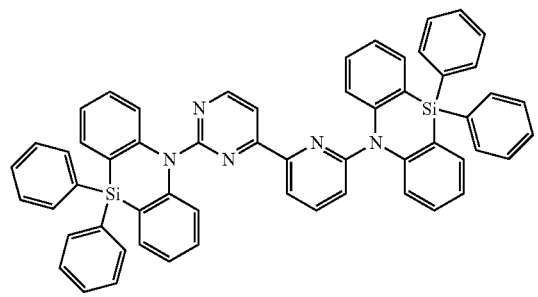
(1-21)
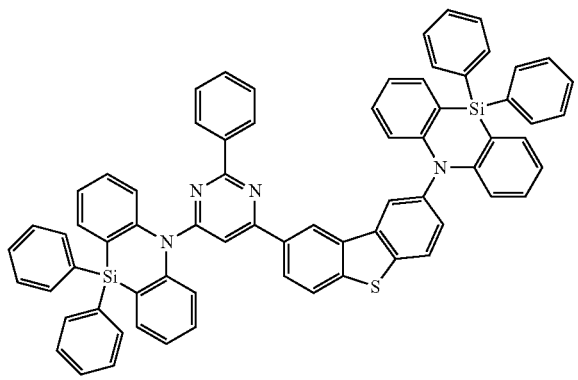
(1-22)
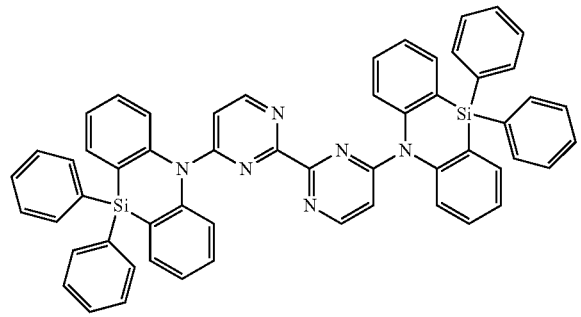
(1-23)
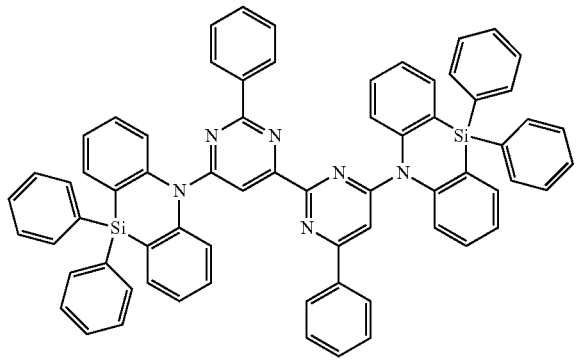
(1-24)
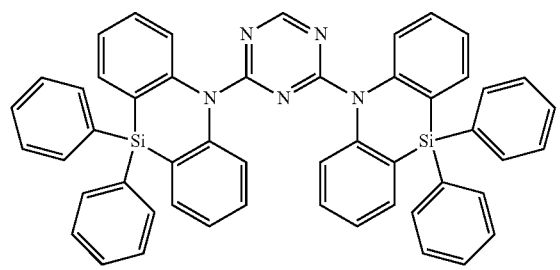
(1-25)
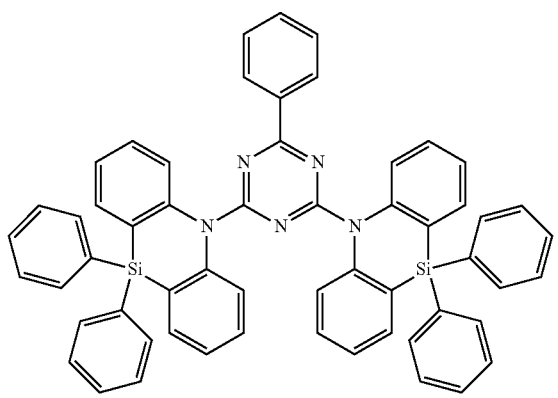

-continued
(1-26)
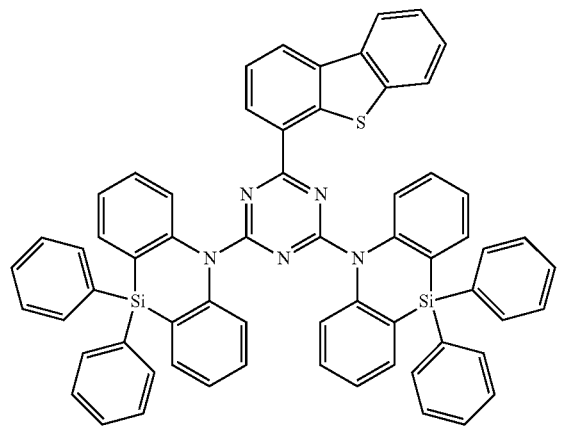
(1-27)
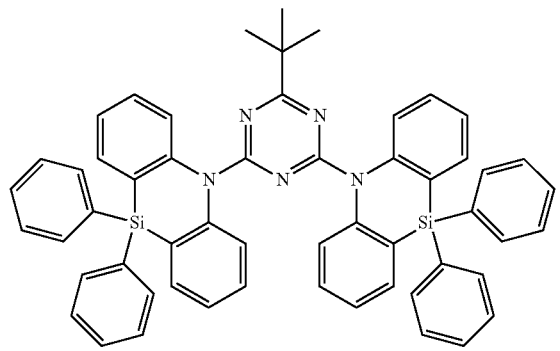
(1-28)
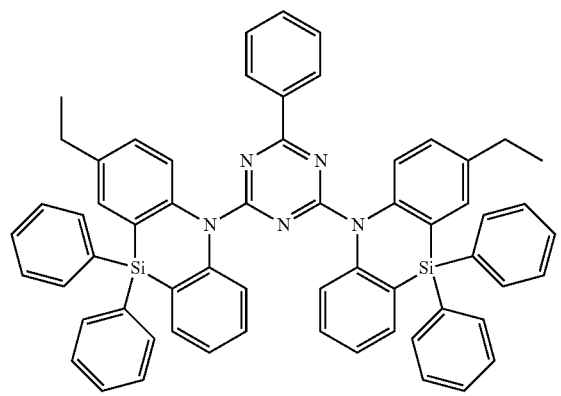
(1-29)
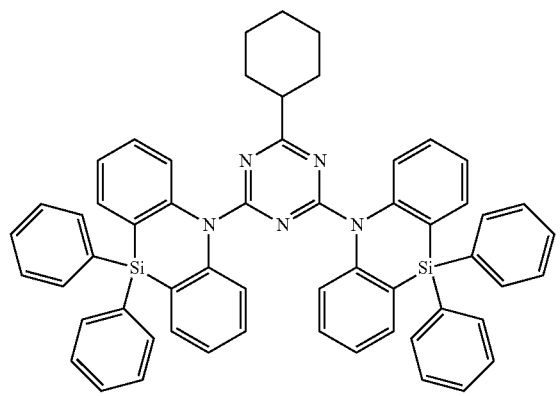
(1-30)
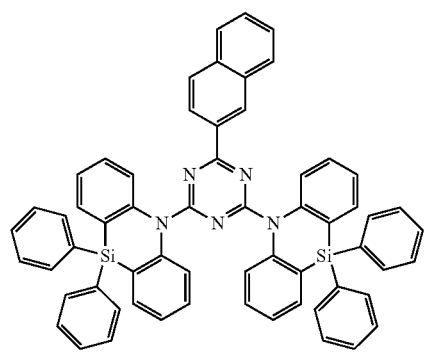
(1-31)
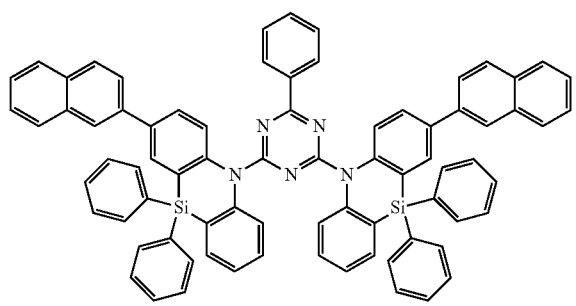
(1-32)
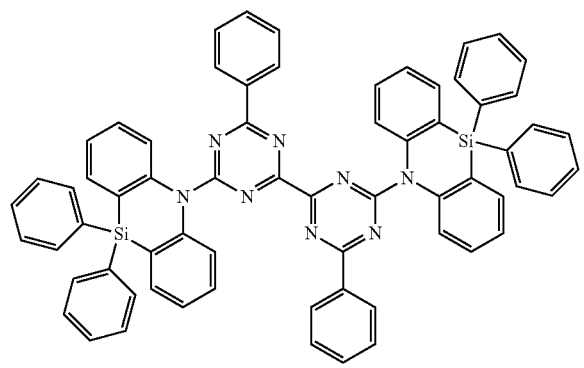
(1-33)
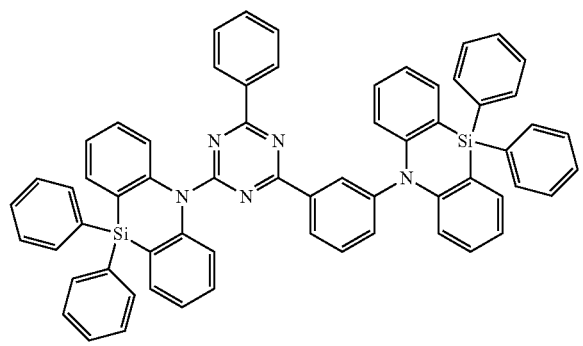

-continued
(1-34)
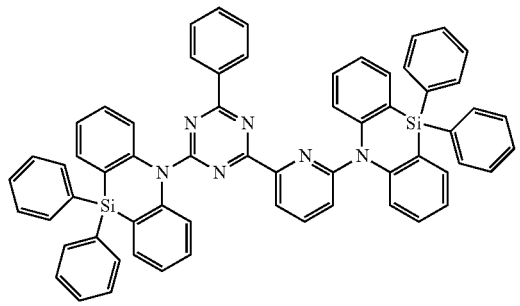
(1-35)
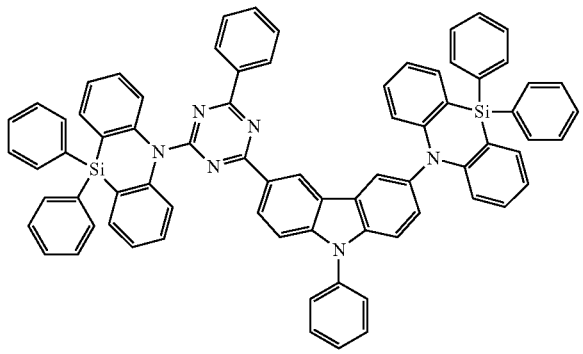
(1-36)
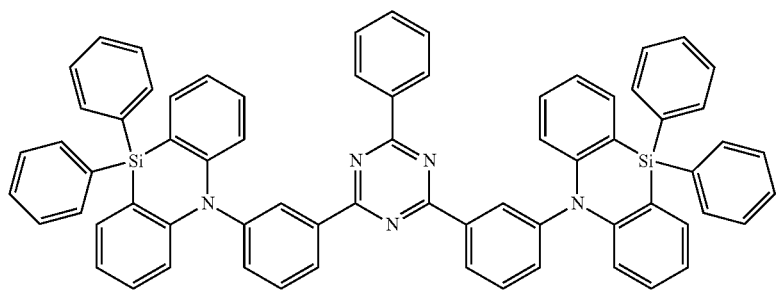
(1-37)
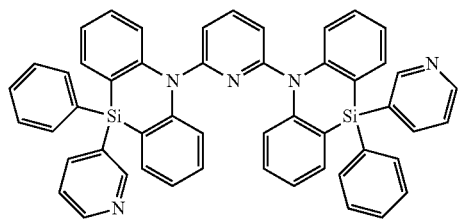
(1-38)
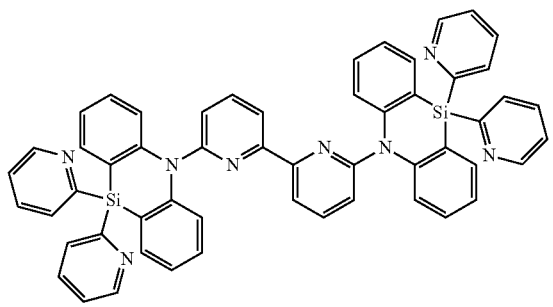
(1-39)
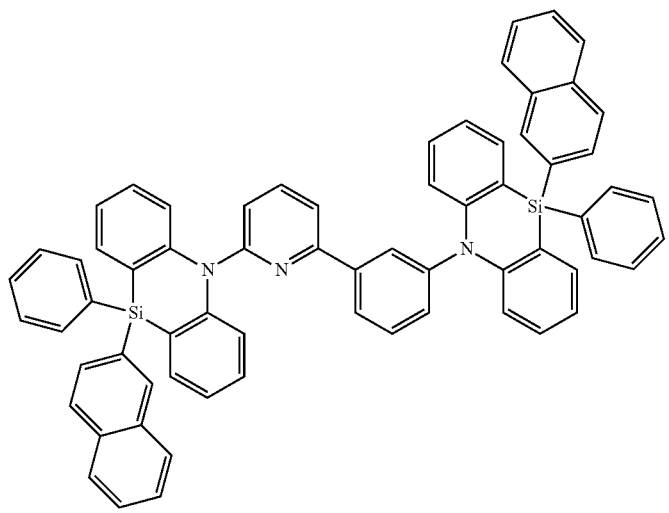

-continued
(1-40)
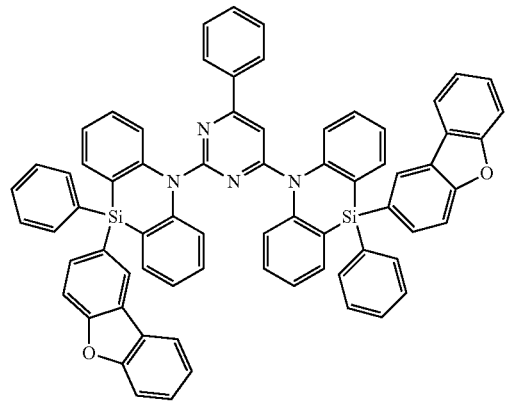
(1-41)
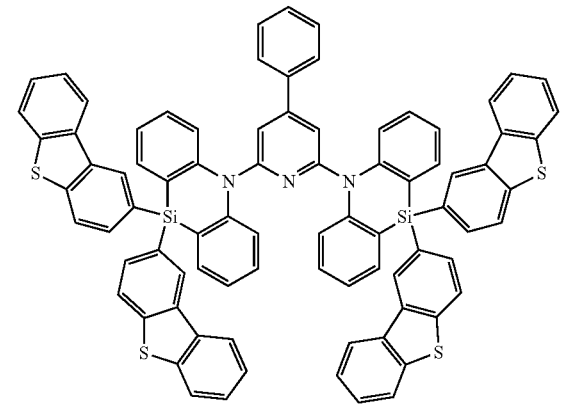
(2-1)
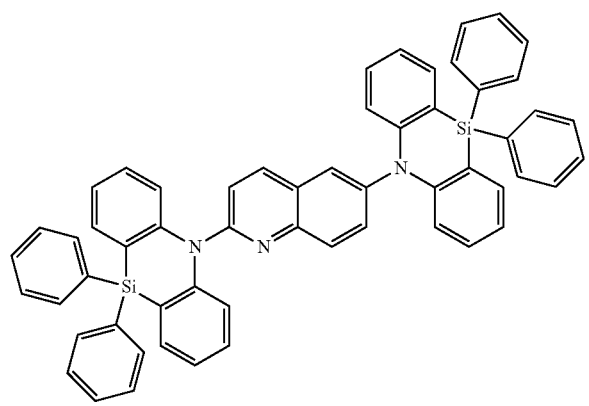
(2-2)
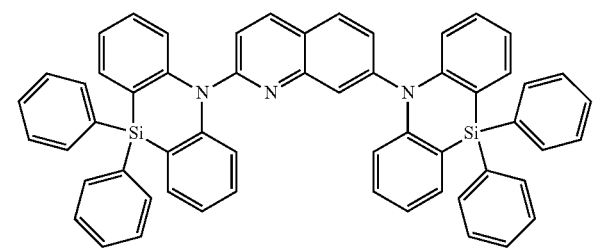
(2-3)
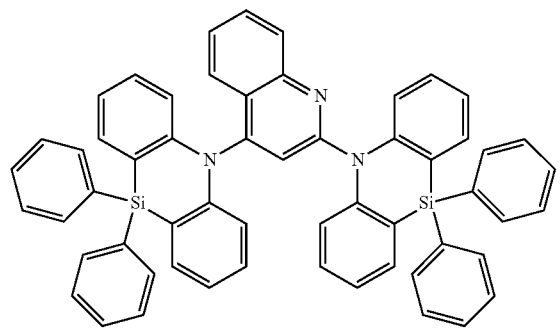
(2-4)
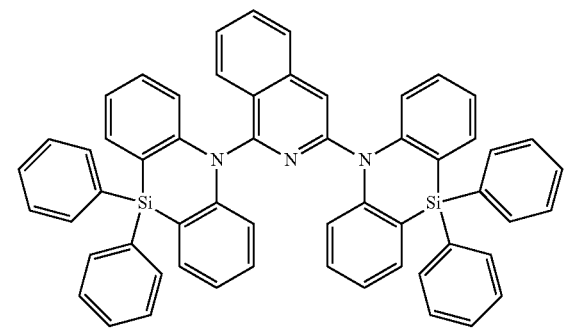
(2-5)
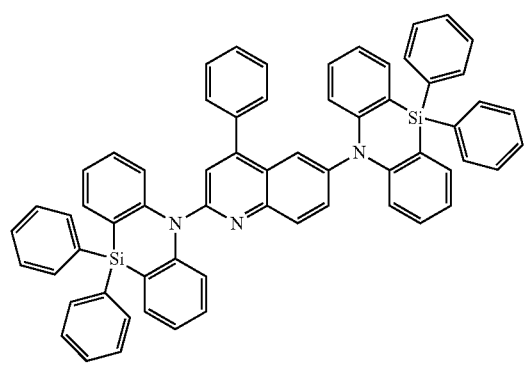
(2-6)
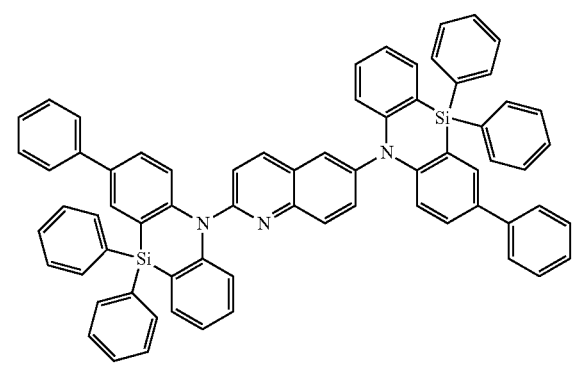

-continued
(2-7)
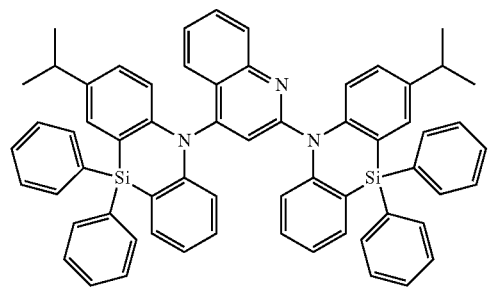
(2-8)
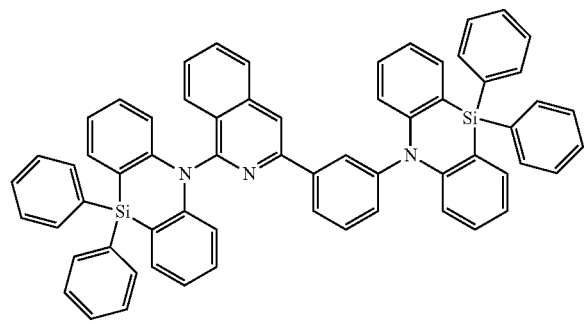
(2-9)
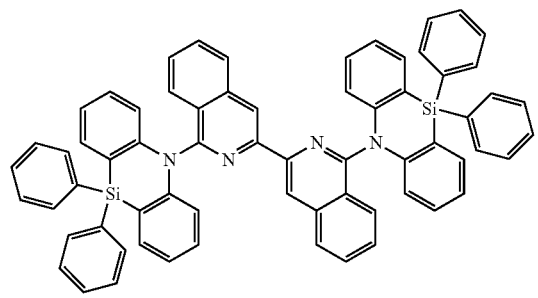
(2-10)
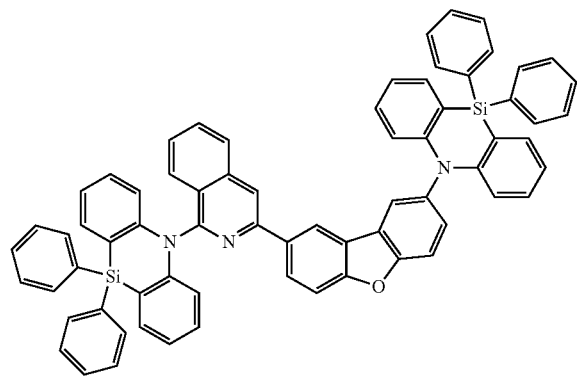
(2-11)
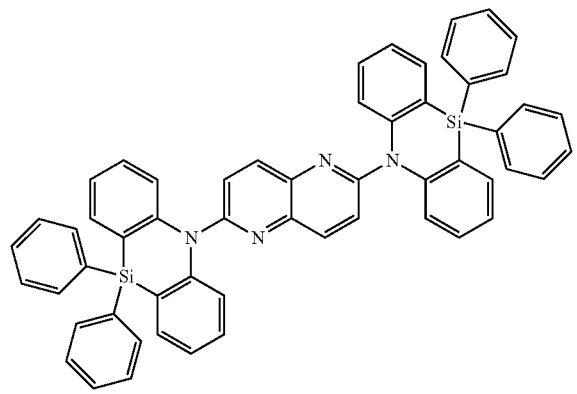
(2-12)
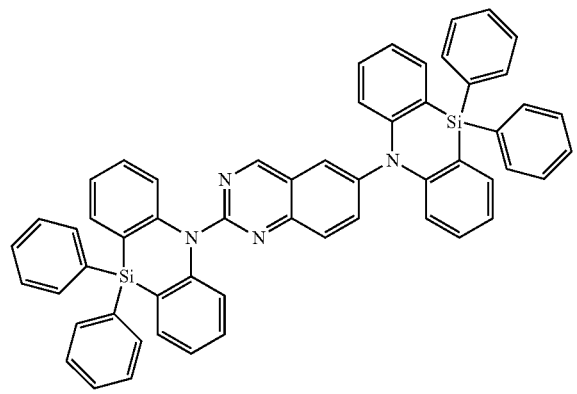
(2-13)
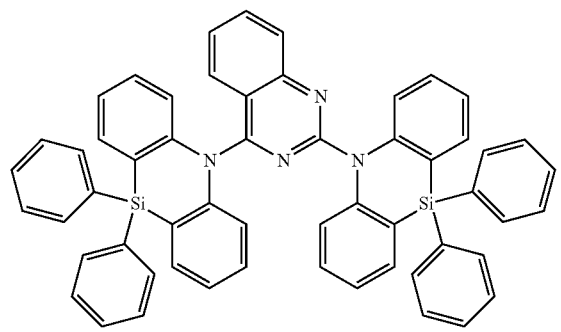
(2-14)
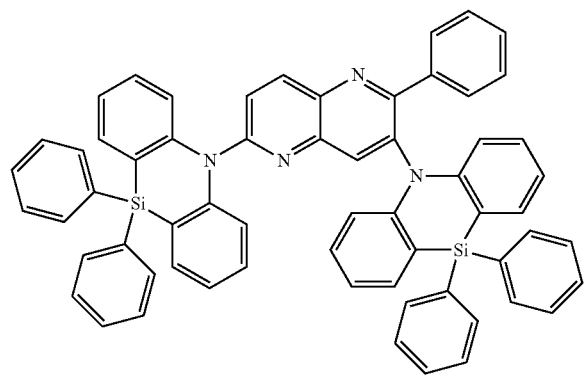

-continued
(2-15)
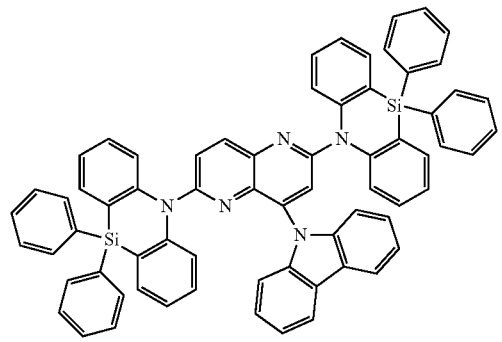
(2-16)
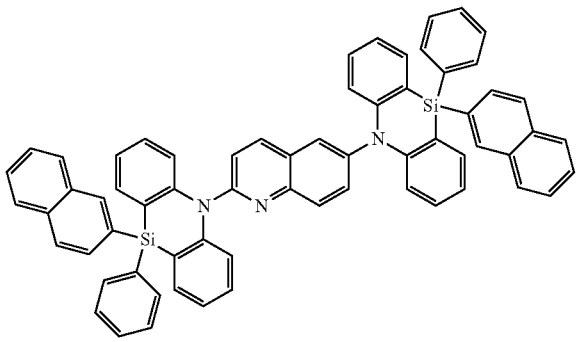
(2-17)
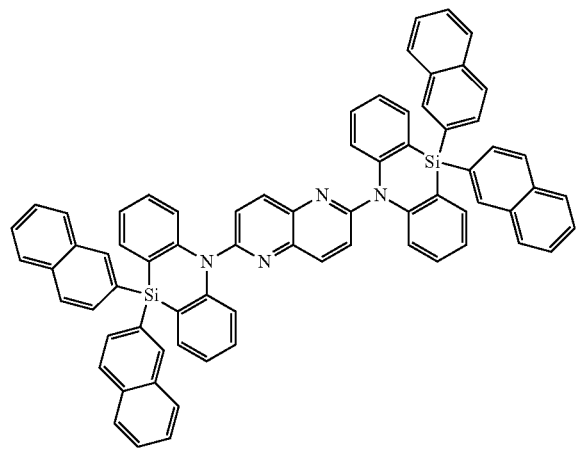
(2-18)
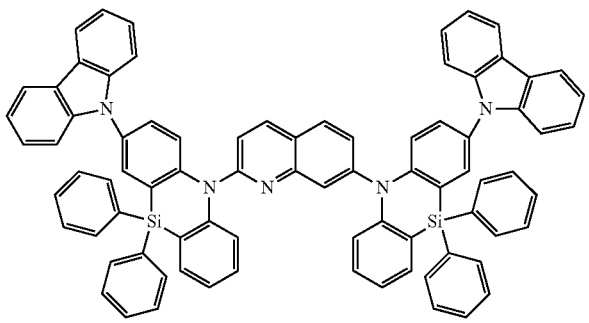
(2-19)
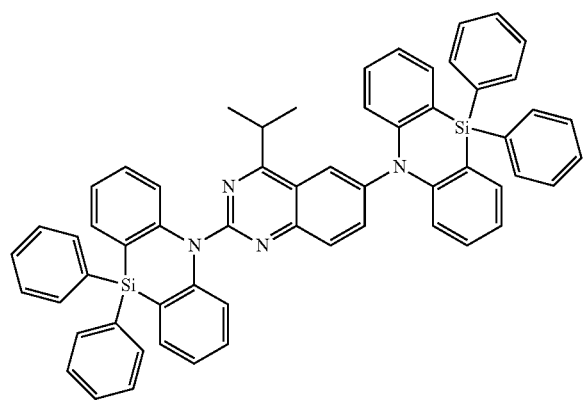
(2-20)
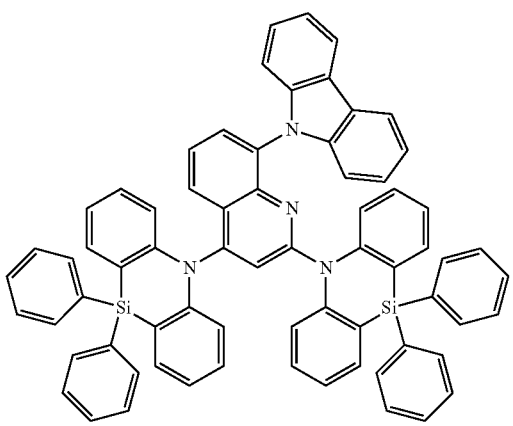

-continued
(2-21)
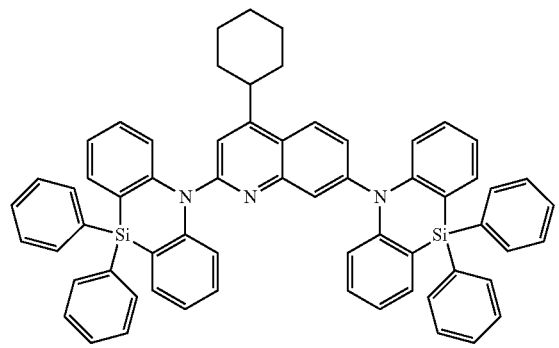
(2-22)
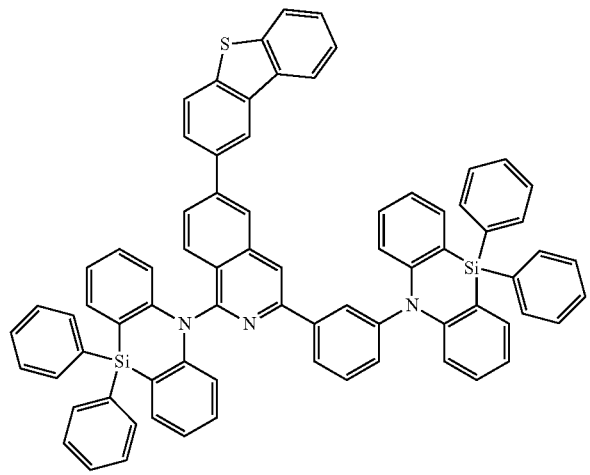
(2-23)
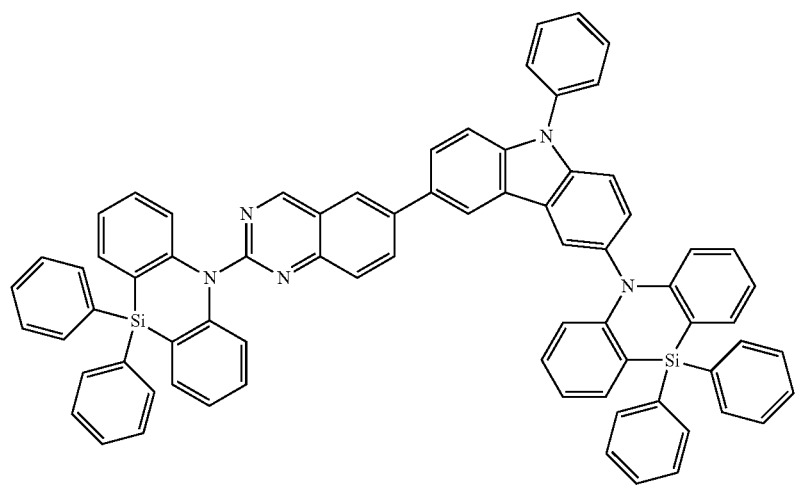
(2-24)
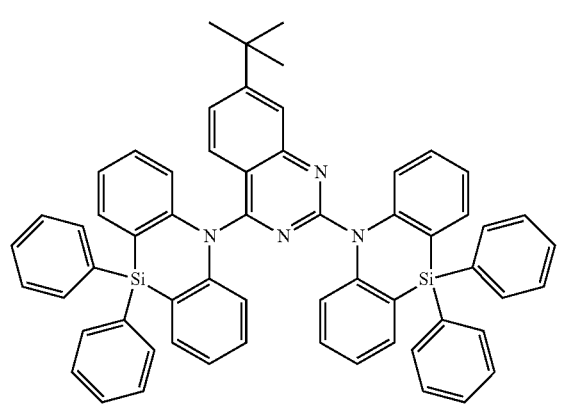
(2-25)
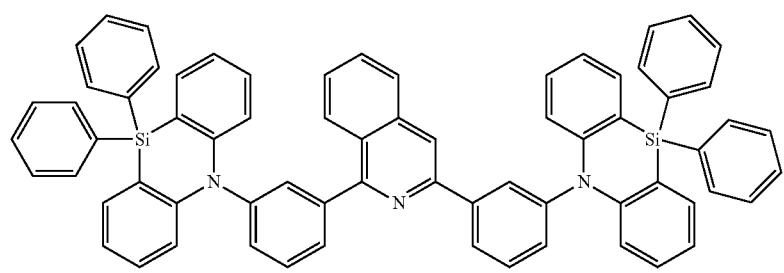

-continued
(3-1)
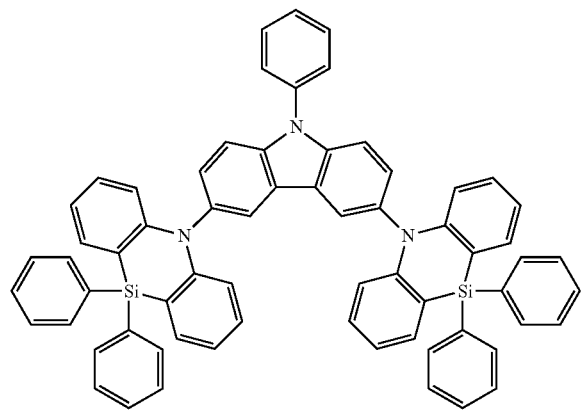
(3-2)
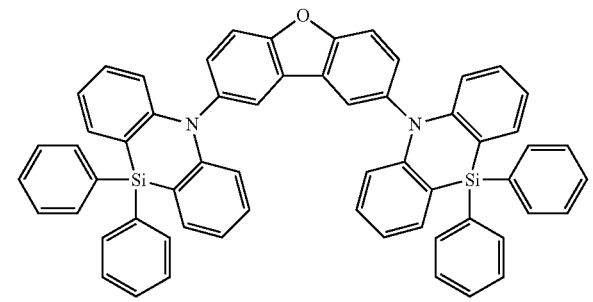
(3-3)
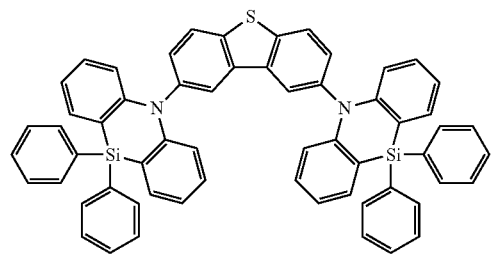
(3-4)
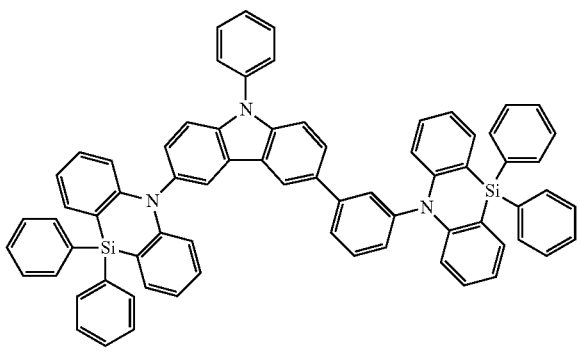
(3-5)
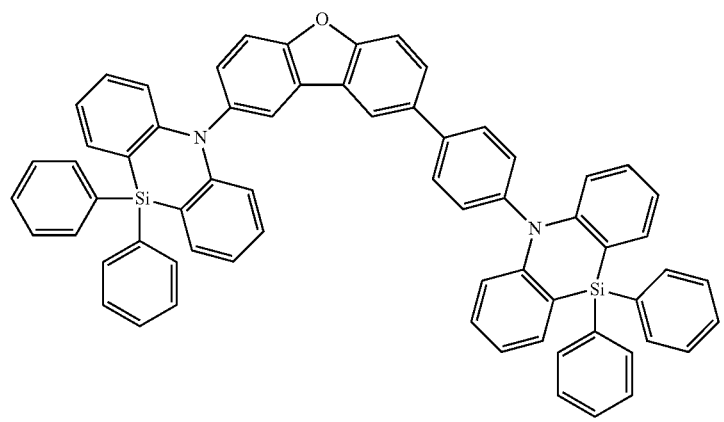
(3-6)
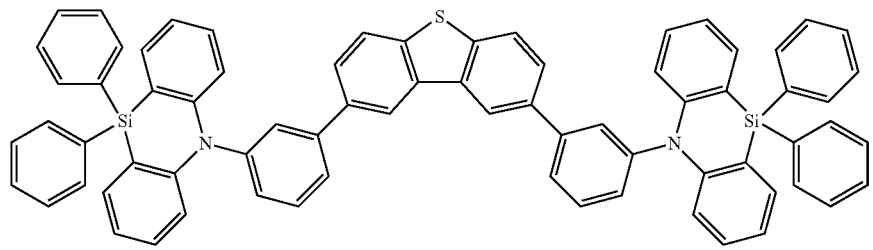

-continued
(3-7)
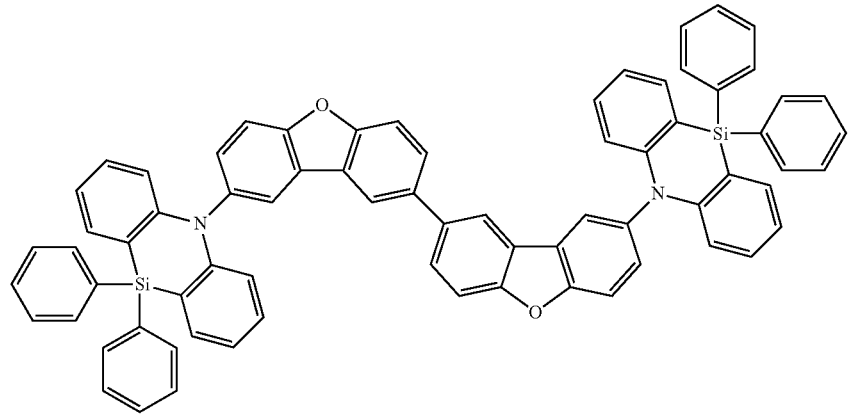
(3-8)
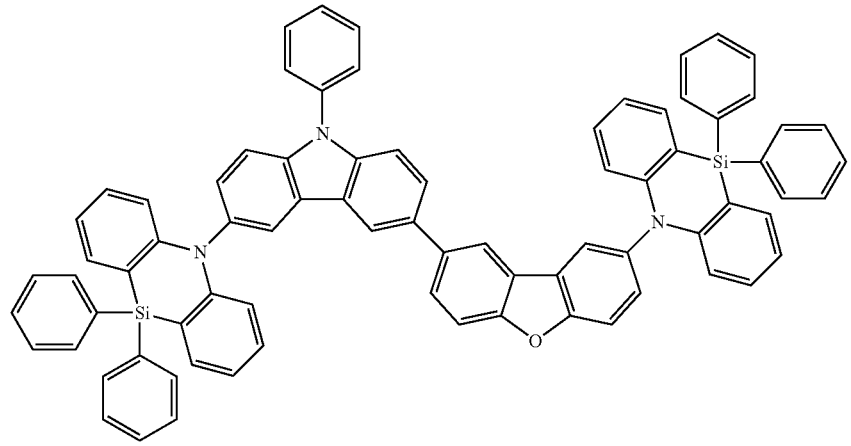
(3-9)
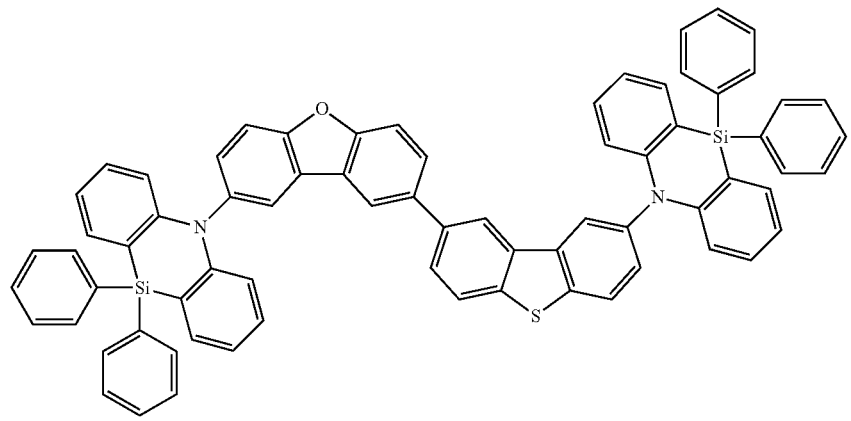
(3-10)
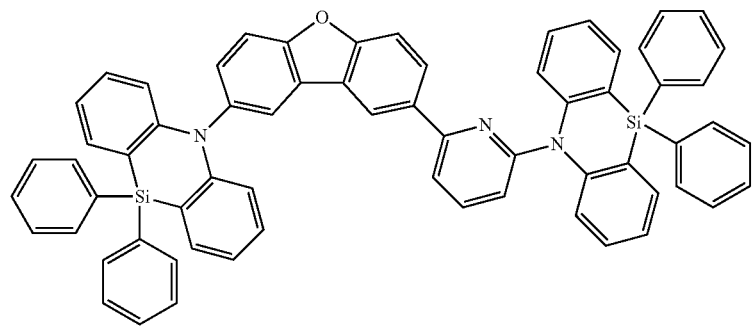

-continued
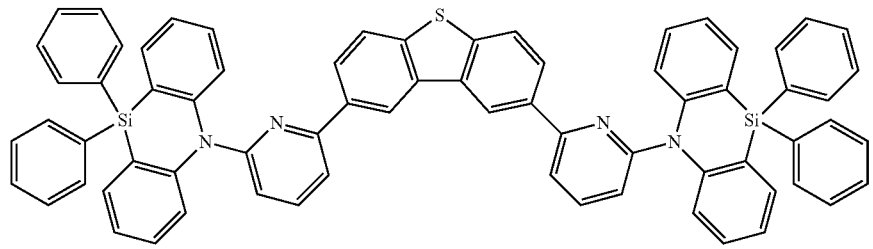
(3-11)
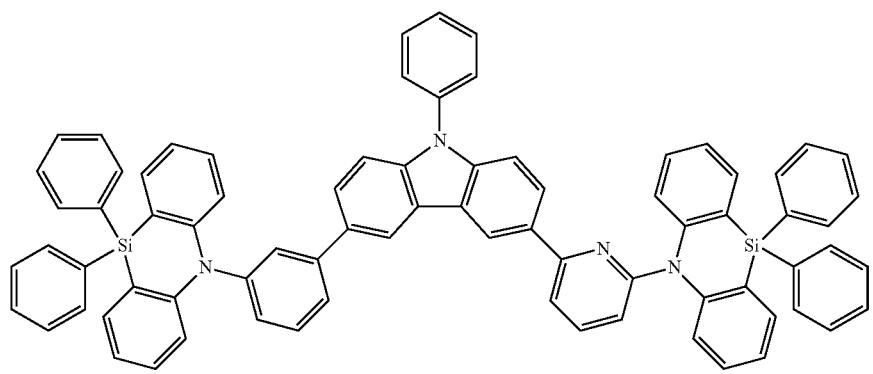
(3-12)
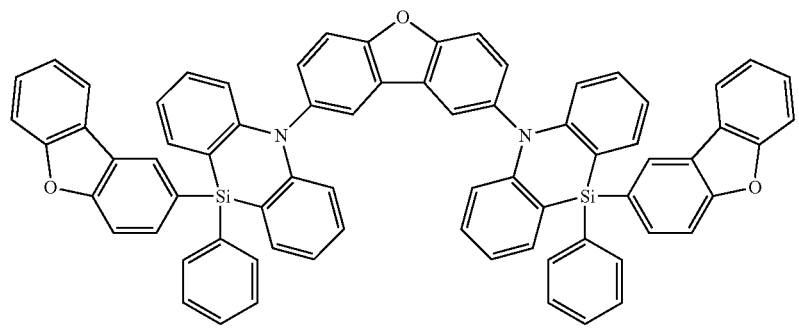
(3-13)
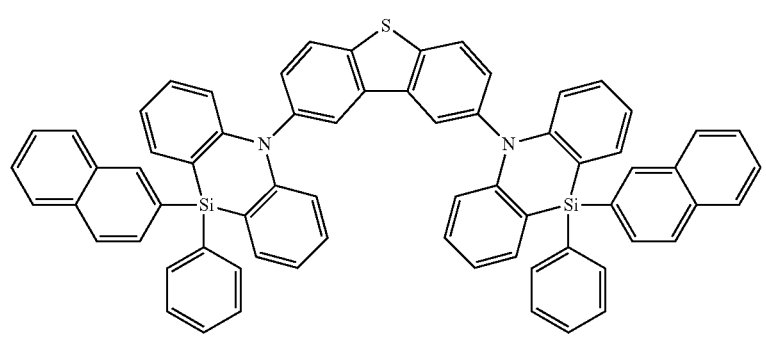
(3-14)

(3-15)
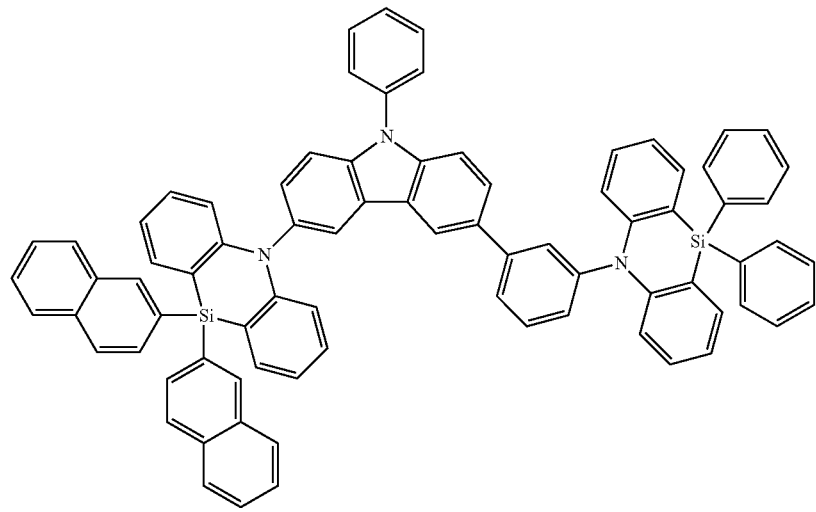
(3-16)
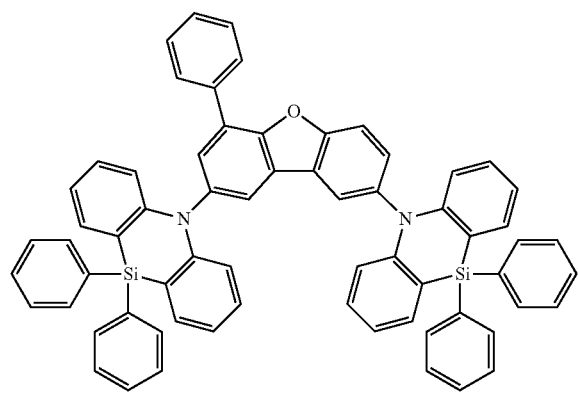
(3-17)
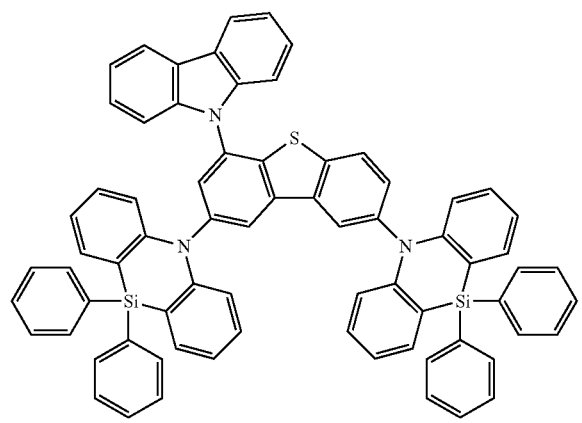
(3-18)
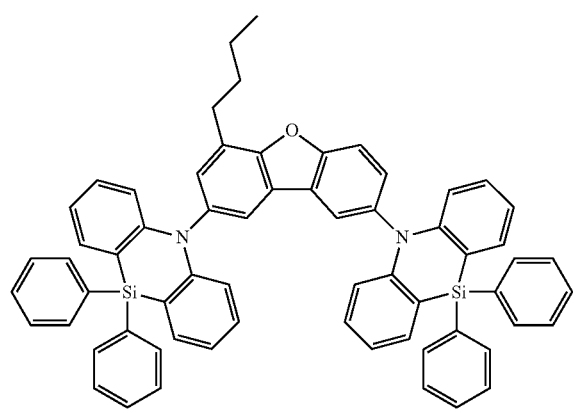
(3-19)
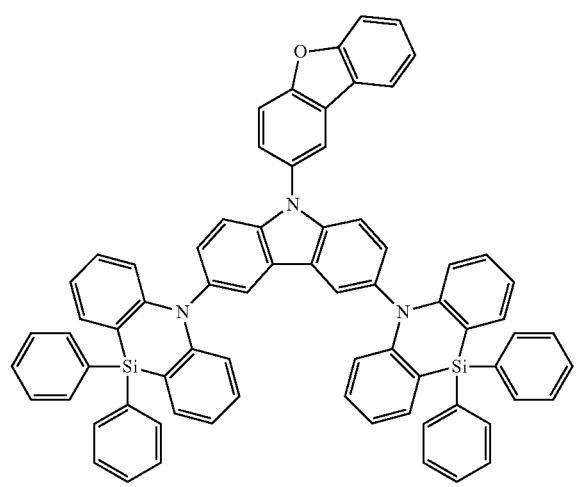

-continued
(3-20)
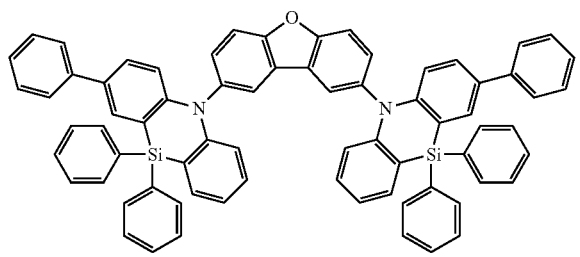
(3-21)
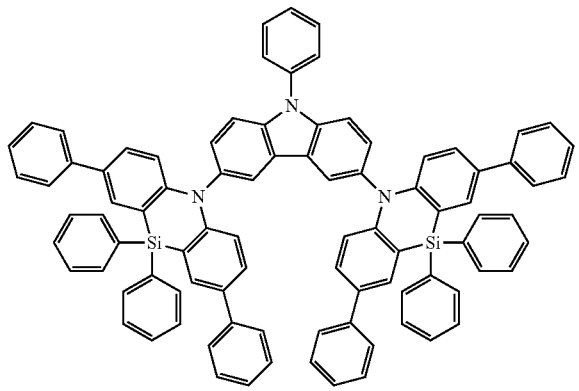
(3-22)
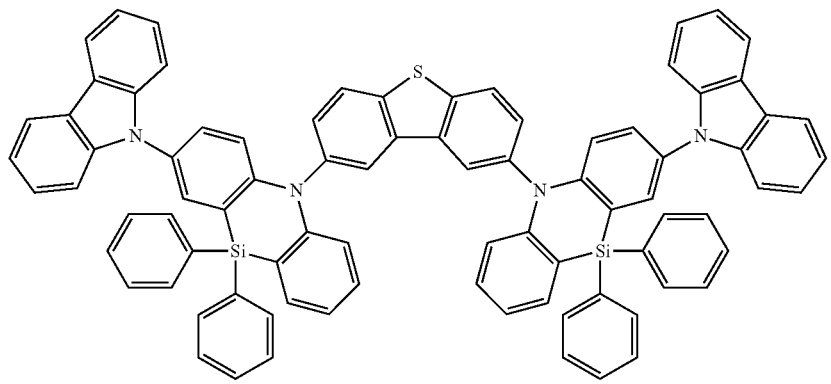
(3-23)
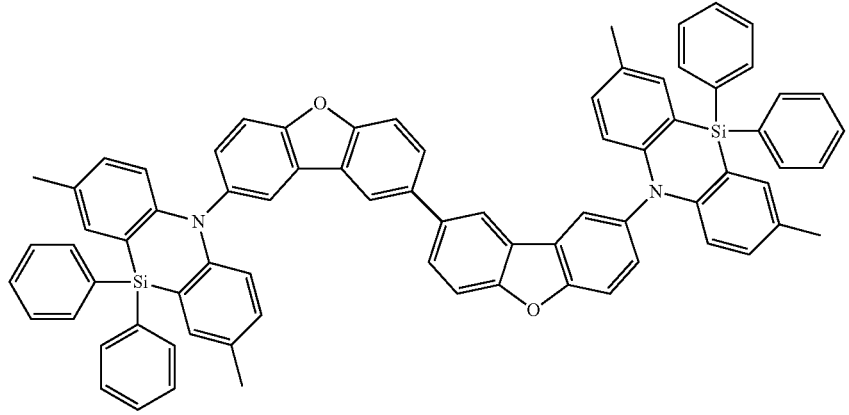
(3-24)
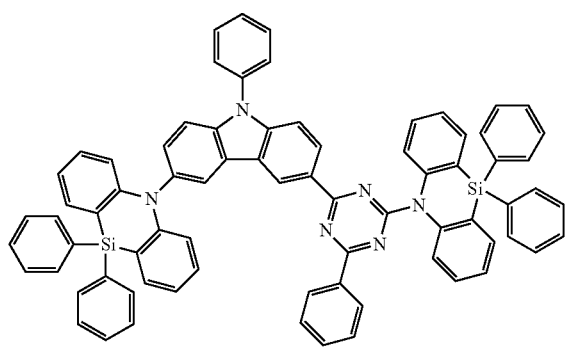
(3-25)
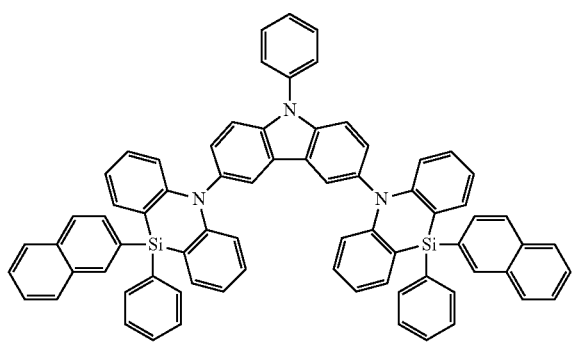

-continued
(3-26)
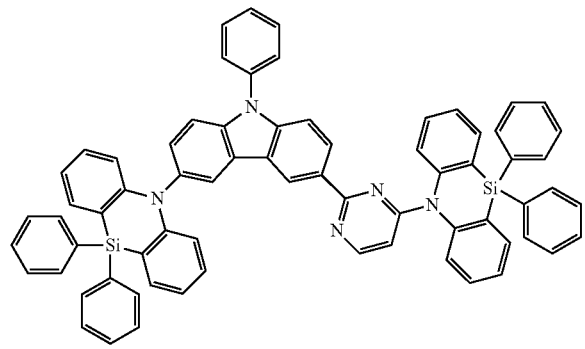
(3-27)
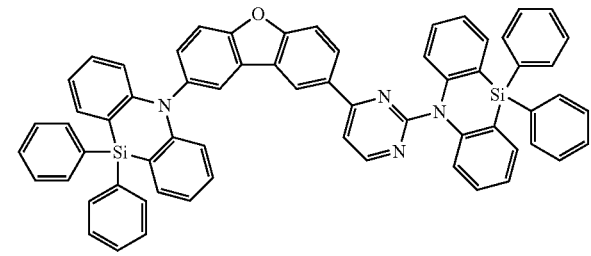
(3-28)
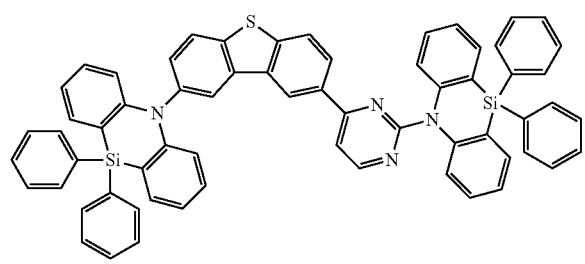
(3-29)
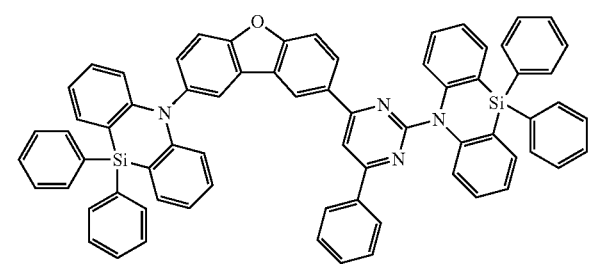
(3-30)
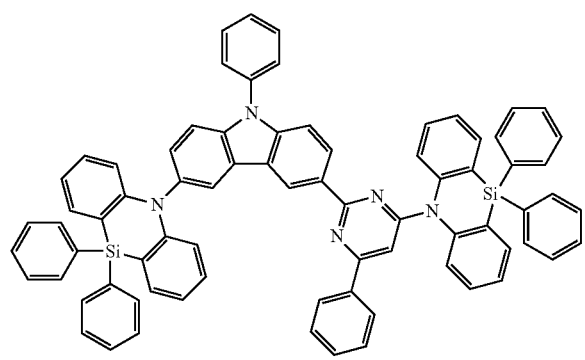
(3-31)
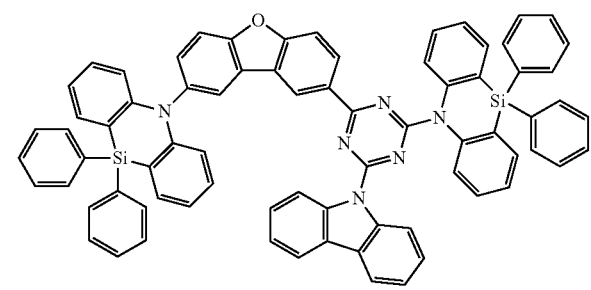
(3-32)
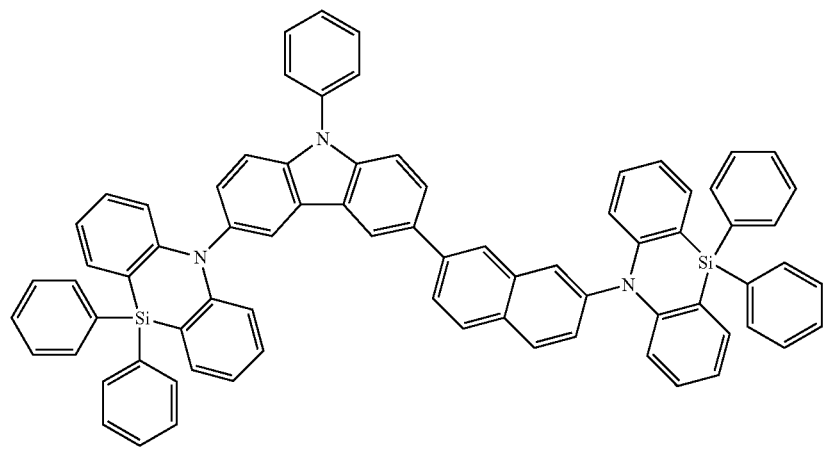

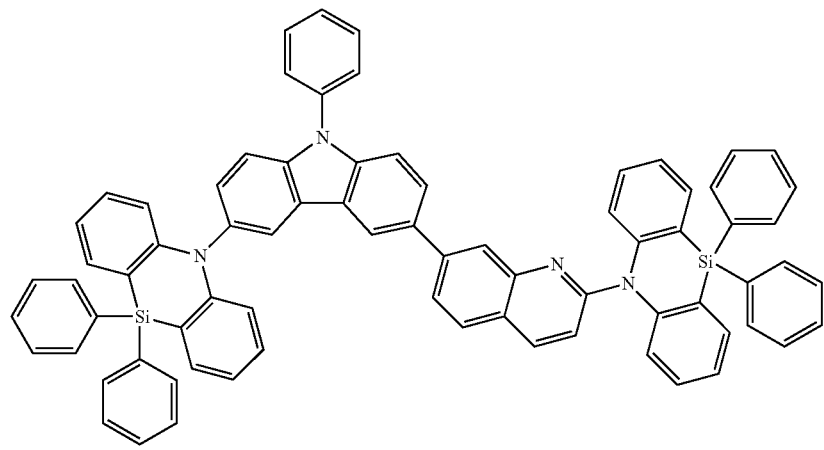

(3-33)

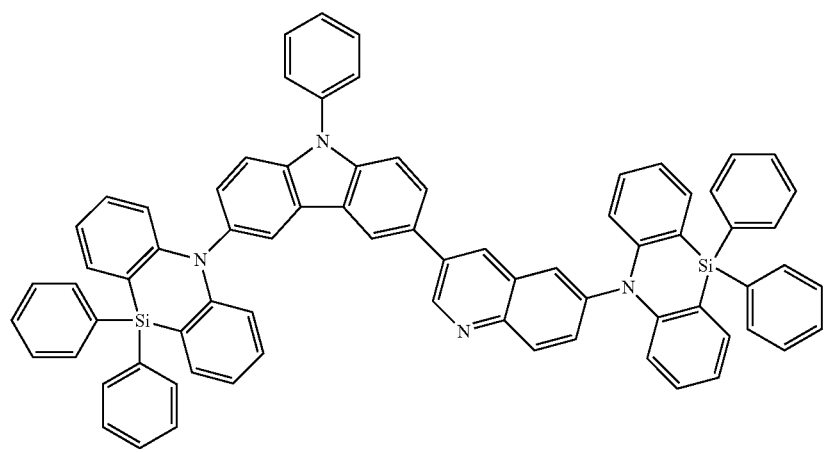

(3-34)

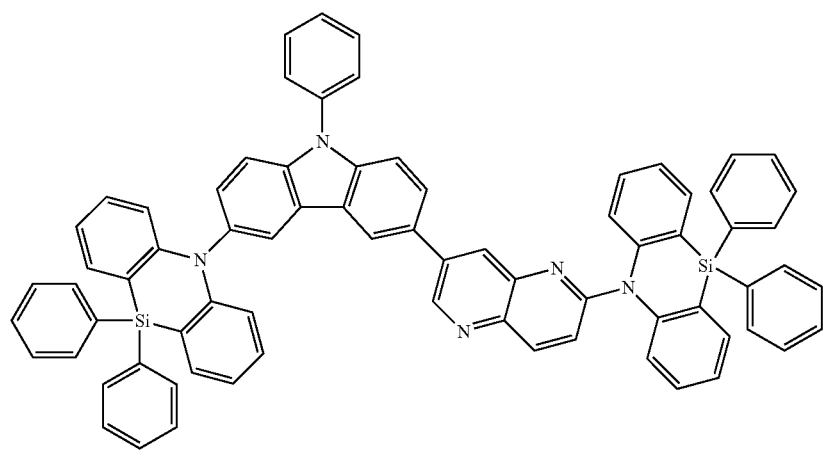

(3-35)

Next, the organic EL device material of the present invention and an organic EL device of the present invention are described. The organic EL device material of the present invention includes the compound of the present invention represented by the general formula (1). The compound represented by the general formula (1) is the organic electroluminescent device material of the present invention.

The organic EL device material of the present invention may be used as a mixture with another organic EL device material, and may contain various dopants. As the dopant, there may be used, for example, a coumarin-, quinacridone-, rubrene-, or stilbene-based derivative, a fluorescent dye, and a noble metal complex such as an iridium complex or a platinum complex.

The organic EL device of the present invention is an organic electroluminescent device, including: a substrate; an anode; at least one organic layer; and a cathode, the anode, the at least one organic layer, and the cathode being laminated on the substrate, in which the at least one organic layer includes an organic layer containing the organic EL device material of the present invention.

Specifically, the organic EL device includes a substrate, an anode, at least one organic layer, and a cathode, the anode, the at least one organic layer, and the cathode being laminated on the substrate, in which the at least one organic layer contains the above-mentioned compound or organic EL device material of the present invention. The organic layer containing the compound of the present invention is preferably at least one layer selected from the group consisting of a light-emitting layer, an electron-transporting layer, a hole-transporting layer, an electron-blocking layer, and a hole-blocking layer, more preferably a light-emitting layer containing a phosphorescent light-emitting dopant.

Next, the structure of the organic EL device of the present invention is described with reference to FIG. 1. However, the structure of the organic EL device of the present invention is by no means limited to one illustrated in FIG. 1.

FIG. 1 is a sectional view illustrating a structural example of a general organic EL device to be used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may have an exciton-blocking layer adjacent to the light-emitting layer, or may have an electron-blocking layer between the light-emitting layer and the hole-injecting layer. The exciton-blocking layer may be inserted on any of the anode side and cathode side of the light-emitting layer, and may also be inserted simultaneously on both sides. The organic EL device of the present invention includes the substrate, the anode, the light-emitting layer, and the cathode as its essential layers. The organic EL device of the present invention preferably has a hole-injecting/transporting layer and an electron-injecting/transporting layer in addition to the essential layers, and more preferably has a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure as compared to FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated as required.

The compound or organic EL device material of the present invention may be used in any layer in the organic EL device, is preferably used in the light-emitting layer, the hole-transporting layer, the electron-blocking layer, the hole-blocking layer, or the electron-transporting layer, and is particularly preferably used as the light-emitting layer, the electron-transporting layer, or the hole-blocking layer.

—Substrate—

The organic EL device of the present invention is preferably supported by a substrate. The substrate is not particularly limited, and any substrate that has long been used for an organic EL device heretofore may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$—ZnO), which may be used for manufacturing an amorphous and transparent conductive film. In order to produce the anode, it may be possible to form any of those electrode substances into a thin film by a method such as vapor deposition or sputtering and form a pattern having a desired shape thereon by photolithography. Alternatively, in the case of not requiring high pattern accuracy (about 100 μm or more), a pattern may be formed via a mask having a desired shape when any of the above-mentioned electrode substances is subjected to vapor deposition or sputtering. Alternatively, when a coatable substance such as an organic conductive compound is used, it is also possible to use a wet film-forming method such as a printing method or a coating method. When luminescence is taken out from the anode, the transmittance of the anode is desirably controlled to more than 10%. Further, the sheet resistance as the anode is preferably several hundred ohms per square ($\Omega/\square$) or less. Further, the thickness of the film is, depending on its material, selected from usually the range of from 10 to 1,000 nm, preferably the range of from 10 to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of electron-injecting property and durability against oxidation or the like. The cathode may be produced by forming any of those electrode substances into a thin film by a method such as vapor deposition or sputtering. Further, the sheet resistance as the cathode is preferably several hundred $\Omega/\square$ or less, and the thickness of the film is selected from usually the range of from 10 nm to 5 μm, preferably the range of from 50 to 200 nm. It should be noted that, in order for luminescence produced to pass through, any one of the anode and cathode of the organic EL device is preferably transparent or semi-transparent, because the light emission luminance improves.

Further, after any of the above-mentioned metals is formed into a film having a thickness of from 1 to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

—Light-Emitting Layer—

The light-emitting layer, which may be any one of a fluorescent light-emitting layer and a phosphorescent light-emitting layer, is preferably the phosphorescent light-emitting layer.

When the light-emitting layer is a fluorescent light-emitting layer, as a fluorescent light-emitting material, at least one kind of fluorescent light-emitting material may be used alone. However, it is preferred that the fluorescent light-emitting material be used as a fluorescent light-emitting dopant and the host material be contained.

The compound of the present invention may be used as the fluorescent light-emitting material in the light-emitting layer. However, when the compound is used for any other organic layer, the fluorescent light-emitting material is known through many patent literatures and the like, and hence may be selected from those in the patent literatures and the like. Examples thereof include: a benzoxazole derivative, a benzimidazole derivative, a benzothiazole derivative, a styrylbenzene derivative, a polyphenyl derivative, a diphenylbutadiene derivative, a tetraphenylbutadiene derivative, a naphthalimide derivative, a coumarin derivative, a fused aromatic compound, a perinone derivative, an oxadiazole derivative, an oxazine derivative, an aldazine derivative, a pyrrolidine derivative, a cyclopentadiene derivative, a bisstyrylanthracene derivative, a quinacridone derivative, a pyrrolopyridine derivative, a thiadiazolopyridine derivative, a cyclopentadiene derivative, a styrylamine derivative, a diketopyrrolopyrrole derivative, and an aromatic dimethylidyne compound; various metal complexes typified by a metal complex of an 8-quinolinol derivative and a metal complex, rare earth metal complex, or transition metal complex of a pyrromethene derivative; polymer compounds such as polythiophene, polyphenylene, and polyphenylene vinylene; and an organic silane derivative. Preferred examples thereof include a fused aromatic compound, a styryl compound, a diketopyrrolopyrrole compound, an oxazine compound, and a metal complex, transition metal complex, or lanthanoid complex of pyrromethene. More preferred examples thereof include naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a, h]anthracene, benzo[a]naphthacene, hexacene, anthanthrene, naphtho[2,1-f]isoquinoline, α-naphthophenanthridine, phenanthroxazole, quinolino[6,5-f]quinoline, and benzothiophanthrene. Each of those materials may have an aryl group, a heteroaromatic ring group, a diarylamino group, or an alkyl group as a substituent.

When the fluorescent light-emitting material is used as the fluorescent light-emitting dopant and the host material is contained, the amount of the fluorescent light-emitting dopant to be incorporated into the light-emitting layer desirably falls within the range of from 0.01 to 20 wt %, preferably from 0.1 to 10 wt %.

In ordinary cases, the organic EL device is caused to emit light by producing a light-emitting substance in an excited state through the injection of charge into a light-emitting substance from each of both electrodes, i.e., the anode and the cathode. It is said that in the case of a charge injection-type organic EL device, 25% of produced excitons are excited to excited singlet states and the remaining 75% are excited to excited triplet states. As known through some literatures, a specific fluorescent light-emitting substance is known to express thermally activated delayed fluorescence via the following mechanism. After the transition of its energy into an excited triplet state through intersystem crossing or the like, the substance undergoes inverse intersystem crossing into an excited singlet state owing to triplet-triplet annihilation or the absorption of thermal energy, thereby radiating fluorescence. The organic EL device using the compound of the present invention can also express delayed fluorescence. In this case, the fluorescence can include both fluorescent emission and delayed fluorescent emission. It should be noted that light emission from the host material may constitute part of the light emission.

When the light-emitting layer is a delayed fluorescent light-emitting layer, a delayed fluorescent light-emitting material may be used alone in the light-emitting layer. However, it is preferred that the delayed fluorescent light-emitting material be used as a delayed fluorescent light-emitting dopant and the host material be mixed.

As the delayed fluorescent light-emitting material in the light emitting layer, the compound of the present invention may be used. However, the delayed fluorescent light-emitting material may be selected from known delayed fluorescent light-emitting materials. Examples thereof include, but not limited to, an indolocarbazole derivative disclosed in the non patent literature Appl. Phys. Lett. 98, 083302 (2011) and a carbazole derivative disclosed in Nature 492, 234 (2012).

Specific examples of the delayed fluorescent light-emitting material are shown below, but the delayed fluorescent light-emitting material is not limited to the following compounds.

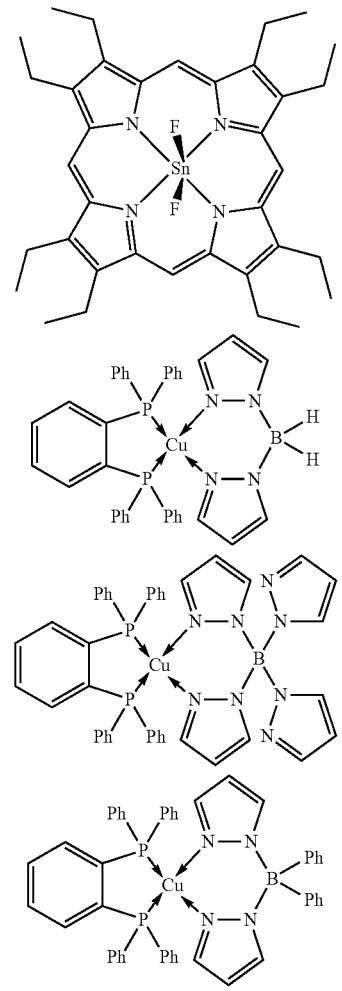

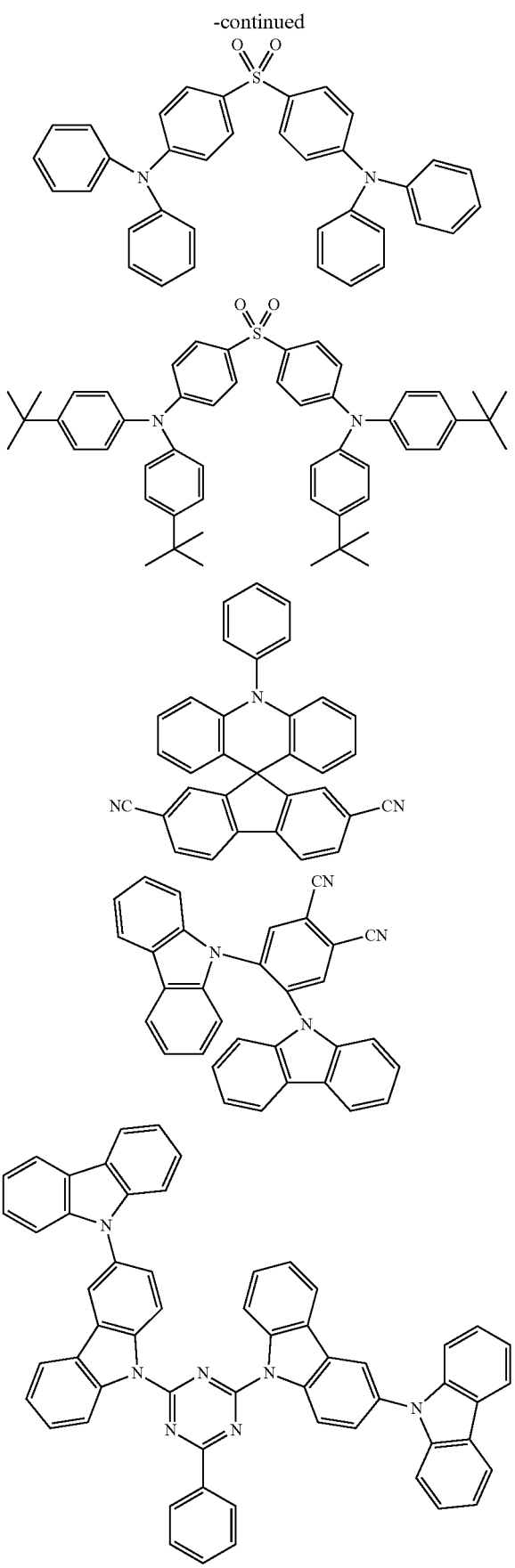
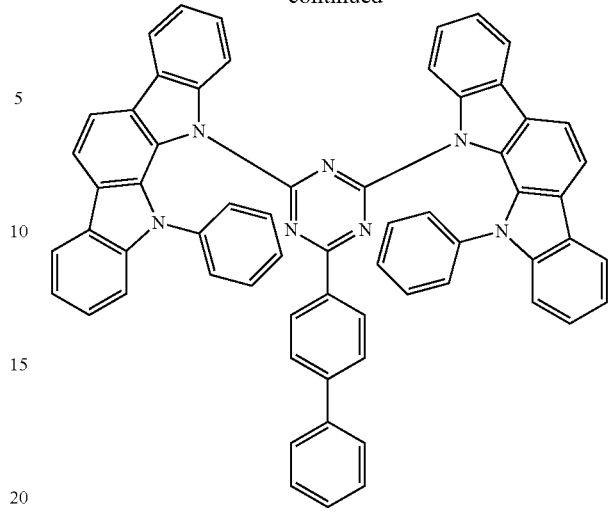

When the delayed fluorescent light-emitting material is used as a delayed fluorescent light-emitting dopant and the host material is contained, the content of the delayed fluorescent light-emitting dopant in the light-emitting layer desirably falls within the range of from 0.01 to 50 wt %, preferably from 0.1 to 20 wt %, more preferably from 0.01 to 10%.

The compound of the present invention may be used as the delayed fluorescent host material in the light-emitting layer. However, the delayed fluorescent host material may be selected from compounds other than the compound of the present invention. For example, the following compound may be used: a compound having a fused aryl ring such as naphthalene, anthracene, phenanthrene, pyrene, chrysene, naphthalene, triphenylene, perylene, fluoranthene, fluorene, or indene, or a derivative thereof; an aromatic amine derivative such as N,N'-dinaphthyl-N,N'-diphenyl-4,4'-diphenyl-1,1'-diamine; a metal chelated oxinoid compound typified by tris(8-quinolinato)aluminum(III); a bisstyryl derivative such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; a thiadiazolopyridine derivative; a dibenzofuran derivative; a carbazole derivative; an indolocarbazole derivative; a triazine derivative; or a polymer-based derivative such as a polyphenylene vinylene derivative, a poly-p-phenylene derivative, a polyfluorene derivative, a polyvinyl carbazole derivative, a polythiophene derivative, or an arylsilane derivative. However, the delayed fluorescent host material is not particularly limited thereto.

When the light-emitting layer is a phosphorescent light-emitting layer, the light-emitting layer contains a phosphorescent light-emitting dopant and a host material. It is recommended to use, as a phosphorescent light-emitting dopant material, a material containing an organic metal complex including at least one metal selected from ruthenium, rhodium, palladium, silver, rhenium, osmium, iridium, platinum, and gold. Specific examples thereof include, but not limited to, the compounds disclosed in the following patent literatures.

For example, WO 2009/073245 A1, WO 2009/046266 A1, WO 2007/095118 A2, WO 2008/156879 A1, WO 2008/140657 A1, US 2008/261076 A1, JP 2008-542203 A, WO 2008/054584 A1, JP 2008-505925 A, JP 2007-522126 A, JP 2004-506305 A, JP 2006-513278 A, JP 2006-50596 A, WO 2006/046980 A1, WO 2005/113704 A2, US 2005/260449 A1, US 2005/2260448A1, US 2005/214576A1, WO 2005/076380A2, US 2005/119485 A1, WO 2004/045001 A2, WO 2004/045000 A2, WO 2006/100888 A1, WO 2007/004380 A1, WO 2007/023659 A1, WO 2008/035664 A1, JP 2003-272861 A, JP 2004-111193 A, JP 2004-319438 A, JP 2007-2080 A, JP 2007-9009 A, JP 2007-227948A, JP 2008-91906 A, JP 2008-311607A, JP 2009-19121 A, JP 2009-46601A, JP 2009-114369A, JP 2003-253128 A, JP 2003-253129 A, JP 2003-253145 A, JP 2005-38847 A, JP 2005-82598 A, JP 2005-139185 A, JP 2005-187473 A, JP 2005-220136A, JP 2006-63080A, JP 2006-104201 A, JP 2006-111623A, JP 2006-213720A, JP 2006-290891A, JP 2006-298899 A, JP 2006-298900 A, WO 2007/018067 A1, WO 2007/058080 A1, WO 2007/058104 A1, JP 2006-131561 A, JP 2008-239565 A, JP 2008-266163 A, JP 2009-57367A, JP 2002-117978A, JP 2003-123982 A, JP 2003-133074 A, JP 2006-93542 A, JP 2006-131524 A, JP 2006-261623 A, JP 2006-303383 A, JP 2006-303394A, JP 2006-310479A, JP 2007-88105A, JP 2007-258550 A, JP 2007-324309A, JP 2008-270737A, JP 2009-96800 A, JP 2009-161524 A, WO 2008/050733 A1, JP 2003-73387A, JP 2004-59433 A, JP 2004-155709 A, JP 2006-104132 A, JP 2008-37848 A, JP 2008-133212 A, JP 2009-57304 A, JP 2009-286716A, JP 2010-83852 A, JP 2009-532546A, JP 2009-536681 A, and JP 2009-542026 A.

Preferred examples of the phosphorescent light-emitting dopant include complexes such as Ir(ppy)3, complexes such as Ir(bt)2.acac3, and complexes such as PtOEt3, the complexes each having a noble metal element such as Ir as a central metal. Specific examples of those complexes are shown below, but the complexes are not limited to the compounds described below.

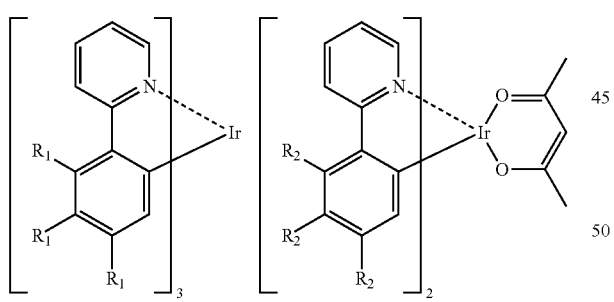

R₁: H, CH₃, CF₃, F       R₂: H, F

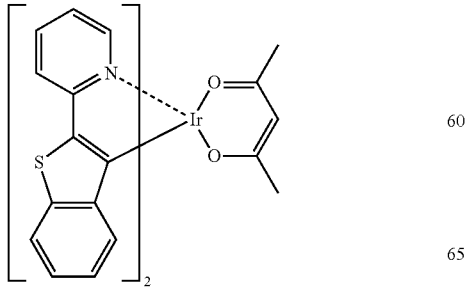

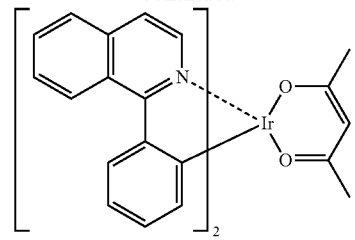

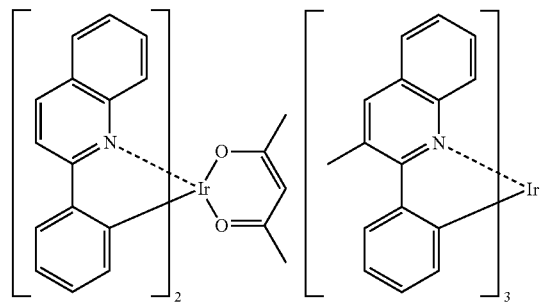

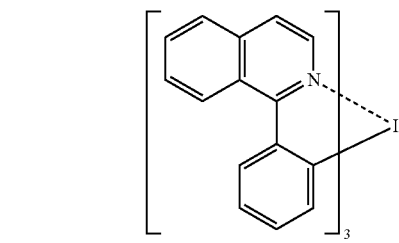

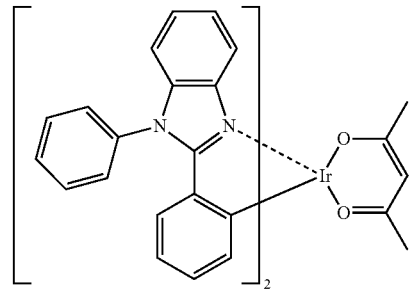

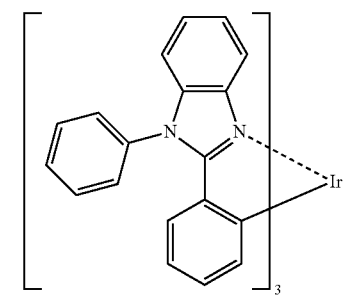

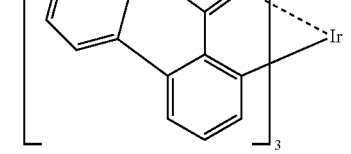

-continued
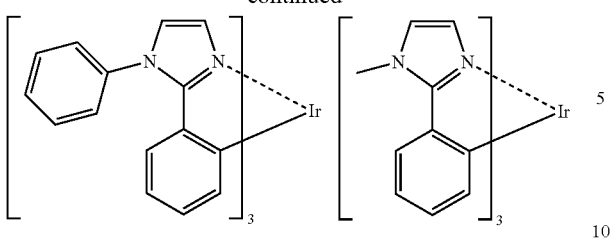
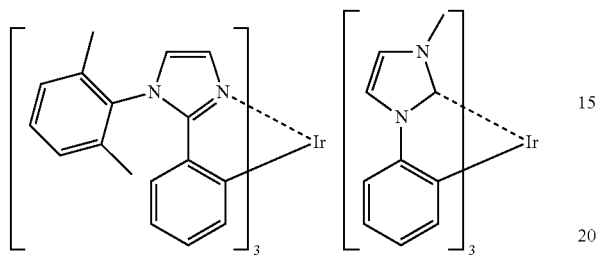
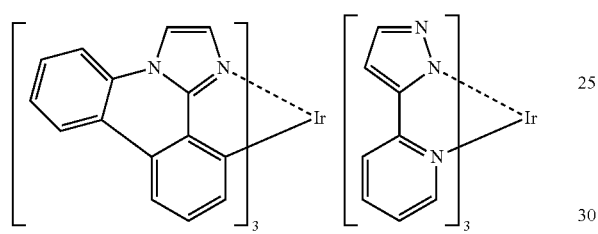
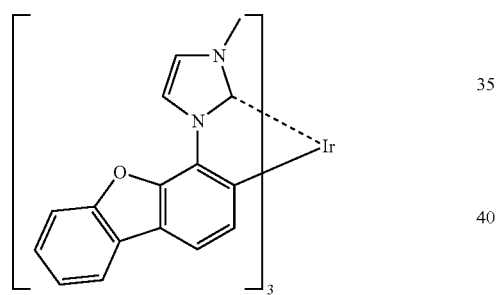
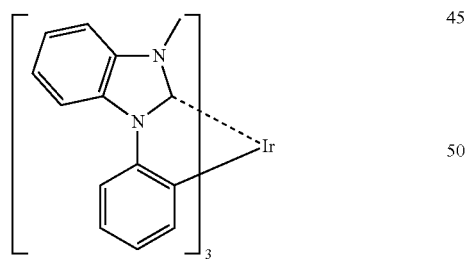
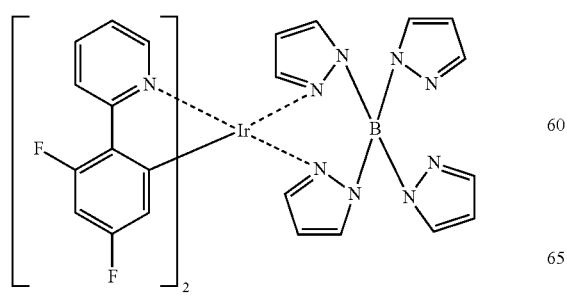
-continued
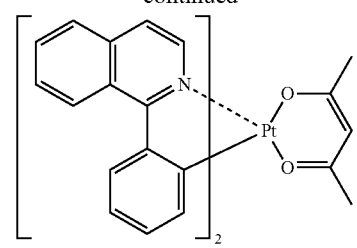
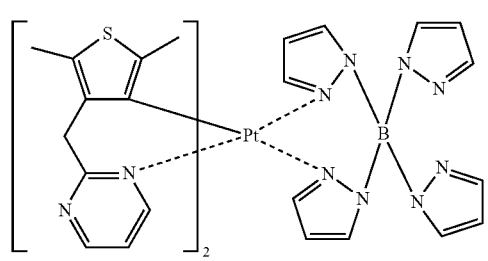
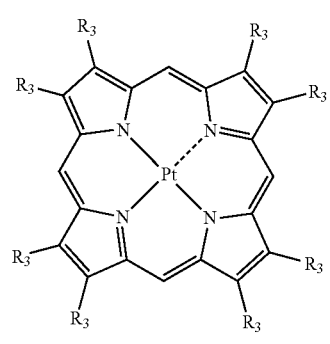
$R_3$: $CH_3$, $CH_2CH_3$
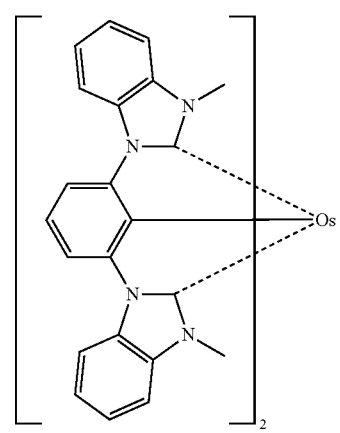
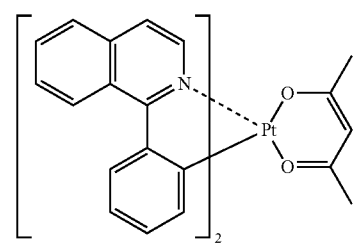

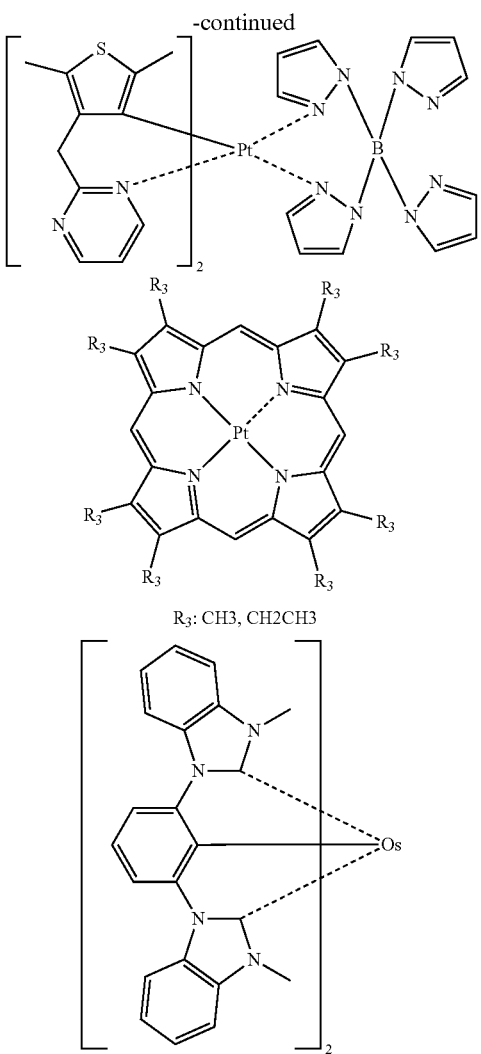

R3: CH3, CH2CH3

It is preferred that the content of the phosphorescent light-emitting dopant in the light-emitting layer fall within the range of from 0.1 to 50 wt %, more preferably from 1 to 30 wt %.

It is preferred to use, as the host material in the light-emitting layer, the compound of the present invention. However, when the compound is used in any of the organic layers other than the light-emitting layer, the material to be used in the light-emitting layer may be any other host material other than the compound of the present invention. In addition, the compound of the present invention and the other host material may be used in combination. Further, a plurality of kinds of known host materials may be used in combination.

It is preferred to use, as a known host compound that may be used, a compound that has a hole-transporting ability or an electron-transporting ability, is capable of preventing luminescence from having a longer wavelength, and has a high glass transition temperature.

Such other host material is known through many patent literatures and the like, and hence may be selected from those in the patent literatures and the like. Specific examples of the host material include, but not particularly limited to, an indole derivative, a carbazole derivative, an indolocarbazole derivative, a triazole derivative, an oxazole deriva- tive, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine derivative, an aromatic dimethylidene-based compound, a porphyrin-based compound, an anthraquinodimethane derivative, an anthrone derivative, a diphenylquinone derivative, a thiopyran dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly (N-vinylcarbazole) derivative, an aniline-based copolymer, a thiophene oligomer, a polythiophene derivative, a polyphenylene derivative, a polyphenylenevinylene derivative, and a polyfluorene derivative.

—Injecting Layer—

The injecting layer refers to a layer formed between an electrode and an organic layer for the purposes of lowering a driving voltage and improving light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be formed as required. The compound of the present invention may be used as an injecting material. However, when the compound is used in any other organic layer, any injecting material selected from conventionally known compounds may be used.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

The compound of the present invention is preferably used in the hole-blocking layer. However, when the compound is used in any other organic layer, a known hole-blocking material may be used. In addition, it is possible to use, as the hole-blocking material, any of materials for the electron-transporting layer to be described later as required.

—Electron-Blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

The compound of the present invention is preferably used as the material for the electron-blocking layer. However, when the compound is used in any other organic layer, a material for the hole-transporting layer to be described later may be used as required. The thickness of the electron-blocking layer is preferably from 3 to 100 nm, preferably from 5 to 30 nm.

—Exciton-Blocking Layer—

The exciton-blocking layer refers to a layer used for blocking excitons produced by the recombination of a hole and an electron in the light-emitting layer from diffusing in charge-transporting layers. The insertion of this layer enables effective confinement of the excitons in the light-emitting layer, thereby being able to improve the luminous efficiency of the device. The exciton-blocking layer may be inserted on any of the anode side and cathode side of the adjacent light-emitting layer, and may also be inserted simultaneously on both sides.

The compound of the present invention represented by the general formula (1) may be used as a material for the exciton-blocking layer. However, when the compound is used in any other organic layer, any material for an exciton-blocking layer selected from conventionally known compounds may be used. Examples thereof include mCP and bis(2-methyl-8-quinolinolato)-4-phenylphenolatoaluminum (III) (BAlq).

—Hole-Transporting Layer—

The hole-transporting layer is formed of a hole-transporting material having a function of transporting holes, and a single hole-transporting layer or a plurality of hole-transporting layers may be formed.

The hole-transporting material has any one of hole-injecting property, hole-transporting property, and electron-blocking property, and any of an organic compound and an inorganic compound may be used. It is preferred to use the compound of the present invention in the hole-transporting layer. However, when the compound is used in any other organic layer, any hole-transporting material selected from conventionally known compounds may be used. Examples of the known hole-transporting material that may be used include a porphyrin compound, an aromatic tertiary amine compound, a styrylamine compound, a triazole derivative, an oxadiazole derivative, an imidazole derivative, a polyarylalkane derivative, a pyrazoline derivative and a pyrazolone derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular oligomer, in particular, a thiophene oligomer. Of those, a porphyrin compound, an aromatic tertiary amine compound, or a styrylamine compound is preferably used, and an aromatic tertiary amine compound is more preferably used.

—Electron-Transporting Layer—

The electron-transporting layer is formed of a material having a function of transporting electrons, and a single electron-transporting layer or a plurality of electron-transporting layers may be formed.

An electron-transporting material (also serving as a hole-blocking material in some cases) only needs to have a function of transferring electrons injected from the cathode into the light-emitting layer. The compound of the present invention is preferably used in the electron-transporting layer. However, when the compound is used in any other organic layer, any electron-transporting material selected from conventionally known compounds may be used. Examples thereof include a nitro-substituted fluorene derivative, a diphenylquinone derivative, a thiopyran dioxide derivative, a carbodiimide, a fluorenylidenemethane derivative, anthraquinodimethane and an anthrone derivative, and an oxadiazole derivative. Further, it is also possible to use, as the electron-transporting material, a thiadiazole derivative prepared by substituting an oxygen atom on an oxadiazole ring with a sulfur atom in the oxadiazole derivative and a quinoxaline derivative that has a quinoxaline ring known as an electron withdrawing group. Further, it is also possible to use a polymer material in which any of those materials is introduced in a polymer chain or is used as a polymer main chain.

EXAMPLES

The present invention is hereinafter described in more detail by way of Examples. However, the present invention is not limited to Examples below and may be carried out in various forms as long as the various forms do not deviate from the gist of the present invention.

The routes described below were used to synthesize compounds of the present invention. It should be noted that the number of each compound corresponds to the number given to the chemical formula in the foregoing.

Example 1

Synthesis of Compound (1-25)

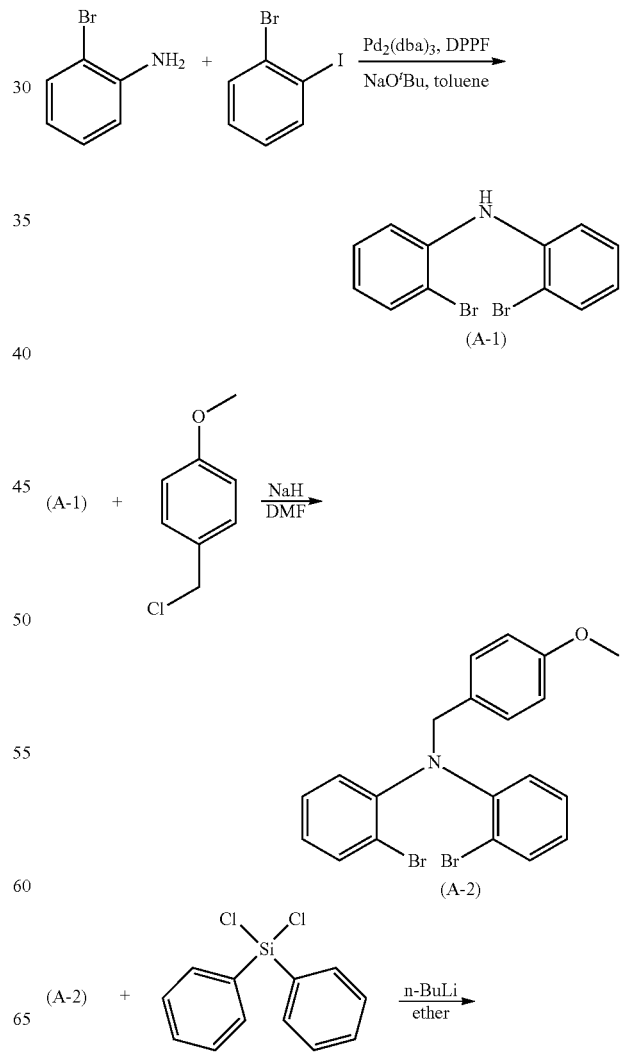

-continued

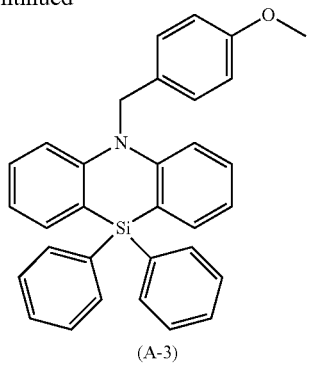

(A-3)

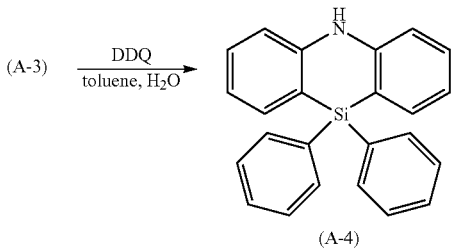

Under a nitrogen atmosphere, 34.4 g (0.20 mol) of 1-amino-2-bromobenzene, 67.9 g (0.24 mol) of 1-bromo-2-iodobenzene, 9.16 g (0.01 mol) of tris(dibenzylideneacetone)dipalladium(0), 11.1 g (0.02 mol) of 1,1'-bis(diphenylphosphino)ferrocene, and 400 ml of toluene were loaded and the mixture was stirred at 120° C. for 3 hr. Subsequently, the reaction solution was cooled to room temperature, an inorganic salt was separated by filtration, and then the solvent was removed by evaporation under reduced pressure. The resultant residue was purified by column chromatography to provide 55.8 g (0.17 mol, 85% yield) of an intermediate (A-1).

Under a nitrogen atmosphere, 7.4 g (0.17 mol) of sodium hydride having a purity of 56.4%, and 150 ml of DMF were loaded and the mixture was stirred at room temperature. 47.5 g (0.15 mol) of the intermediate (A-1) dissolved in 200 ml of DMF were added dropwise thereto, and the mixture was stirred for 1 hr. 25.0 g (0.16 mol) of p-methoxybenzyl chloride dissolved in 150 ml of DMF were added dropwise thereto, and the mixture was stirred at room temperature for 14 hr. After that, 2,000 ml of distilled water were added and the precipitated solid was separated by filtration. The solid that had been separated by filtration was dissolved in dichloromethane, and the organic layer was washed with distilled water (2×100 ml). After that, the resultant organic layer was dried over anhydrous magnesium sulfate, and then the solvent was removed by evaporation under reduced pressure. The resultant residue was purified by column chromatography to provide 58.8 g (0.13 mol, 88% yield) of an intermediate (A-2).

Under a nitrogen atmosphere, 56.0 g (0.125 mol) of the intermediate (A-2) and 400 ml of ether were loaded and the mixture was stirred. The mixture was cooled to 0° C., and 100 ml (0.269 mol) of 2.69 M n-BuLi/hex were added dropwise thereto. Stirring was continued at 0° C. for 0.5 hr, and then 33.2 g (0.131 mol) of dichlorodiphenylsilane dissolved in 100 ml of ether were added dropwise. After that, the mixture was stirred at room temperature for 2 hr. Subsequently, the solvent was removed by evaporation under reduced pressure, the residue was dissolved in ethyl acetate, and the organic layer was washed with distilled water (2×100 ml). After that, the resultant organic layer was dried over anhydrous magnesium sulfate, and then the solvent was removed by evaporation under reduced pressure. The resultant residue was purified by column chromatography to provide 53.3 g (0.11 mol, 91% yield) of an intermediate (A-3).

Under a nitrogen atmosphere, 50.0 g (0.11 mol) of the intermediate (A-3), 26.5 g (0.12 mol) of 2,3-dichloro-5,6-dicyano-1,4-benzoquinone, 500 ml of toluene, and 50 ml of distilled water were loaded and the mixture was stirred at 80° C. for 14 hr. After that, the solvent was removed by evaporation under reduced pressure, the residue was dissolved in ethyl acetate, and the organic layer was washed with distilled water (2×100 ml). After that, the resultant organic layer was dried over anhydrous magnesium sulfate, and then the solvent was removed by evaporation under reduced pressure. The resultant residue was purified by column chromatography to provide 17.7 g (0.051 mol, 48% yield) of an intermediate (A-4).

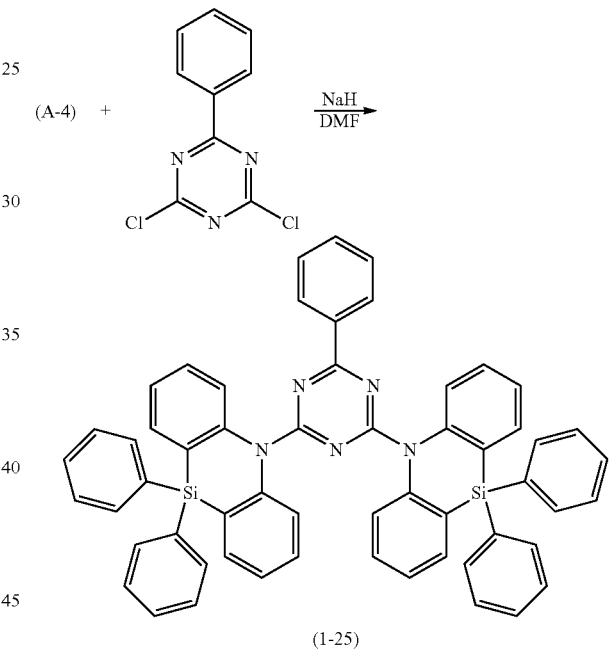

Under a nitrogen atmosphere, 1.1 g (0.027 mol) of sodium hydride having a purity of 56.40, and 50 ml of DMF were loaded and the mixture was stirred at room temperature. 7.8 g (0.022 mol) of the intermediate (A-4) dissolved in 100 ml of DMF were added dropwise thereto, and the mixture was stirred for 0.5 hr. 2.4 g (0.011 mol) of dichlorophenyltriazine dissolved in 50 ml of DMF were added dropwise thereto, and the mixture was stirred at room temperature for 8 hr. After that, 1,000 ml of distilled water were added and the precipitated solid was separated by filtration. The solid that had been separated by filtration was dissolved in dichloromethane, and the organic layer was washed with distilled water (2×100 ml). After that, the resultant organic layer was dried over anhydrous magnesium sulfate, and then the solvent was removed by evaporation under reduced pressure. The resultant residue was purified by column chromatography to provide 2.5 g (0.003 mol, 28% yield) of a compound (1-25).

APCI-TOFMS, m/z 852 [M+H]+

Figure 2:
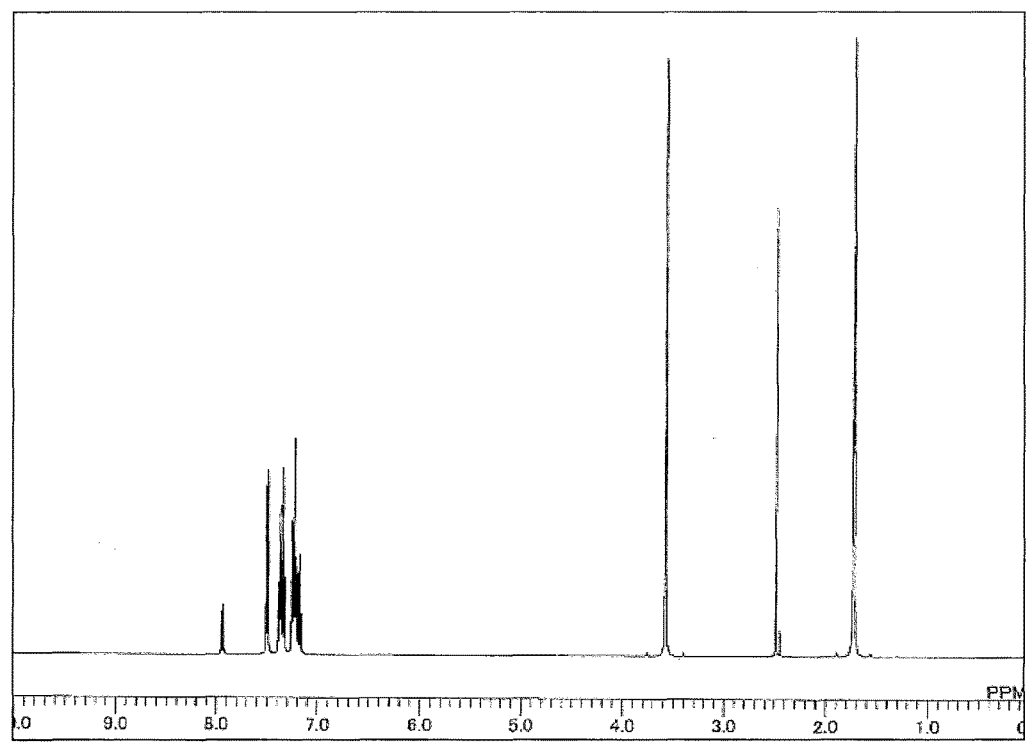
FIG. 2 shows a $^1$H-NMR chart of a compound (1-25).

FIG. 2 shows the $^1$H-NMR measurement result (measurement solvent: THF-d8) of the compound (1-25).

Example 2

Synthesis of Compound (1-1)

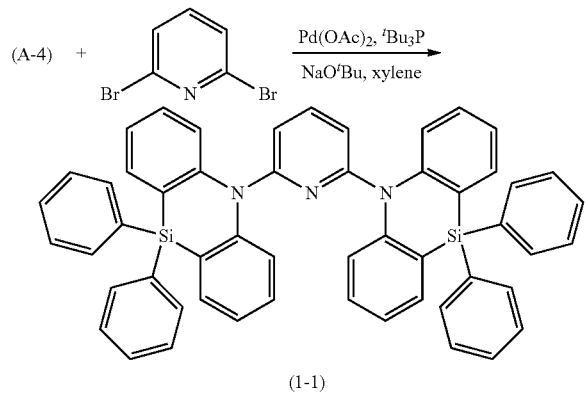

(1-1)

Under a nitrogen atmosphere, 0.05 g (0.00023 mol) of palladium acetate and 8 ml of xylene were loaded and the mixture was stirred at room temperature. 0.19 g (0.00092 mol) of t-butylphosphine was added thereto and the mixture was stirred at 80° C. for 1 hr. Separately, under a nitrogen atmosphere, 8.0 g (0.023 mol) of the intermediate (A-4), 1.51 g (0.011 mol) of 2,6-dibromopyridine, 4.4 g (0.046 mol) of sodium-t-butoxide, and 80 ml of xylene were loaded and the mixture was stirred at 80° C. The previously prepared solution was added thereto, and the mixture was stirred at 145° C. for 2 hr. Subsequently, the reaction solution was cooled to room temperature, an inorganic salt was separated by filtration, and then the solvent was removed by evaporation under reduced pressure. The resultant residue was purified by column chromatography to provide 7.6 g (0.01 mol, 89% yield) of a compound (1-1).

APCI-TOFMS, m/z 774 [M+H]+

Example 3

Synthesis of Compound (3-2)

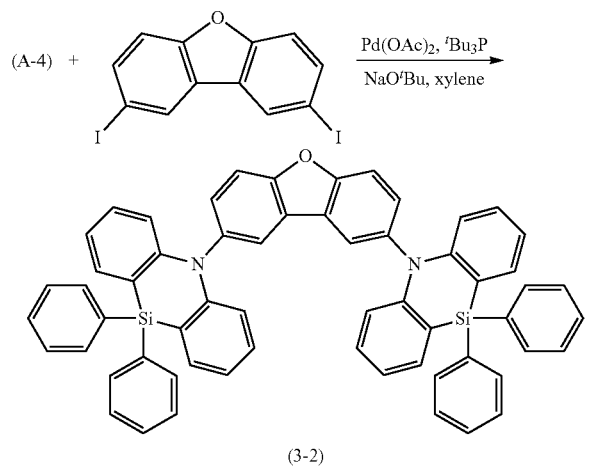

(3-2)

Under a nitrogen atmosphere, 0.08 g (0.00036 mol) of palladium acetate and 10 ml of xylene were loaded and the mixture was stirred at room temperature. 0.29 g (0.0014 mol) of t-butylphosphine was added thereto and the mixture was stirred at 80° C. for 1 hr. Separately, under a nitrogen atmosphere, 12.6 g (0.036 mol) of the intermediate (A-4), 7.11 g (0.017 mol) of 2,8-diiododibenzofuran, 6.92 g (0.072 mol) of sodium-t-butoxide, and 100 ml of xylene were loaded and the mixture was stirred at 80° C. The previously prepared solution was added thereto, and the mixture was stirred at 145° C. for 2 hr. Subsequently, the reaction solution was cooled to room temperature, an inorganic salt was separated by filtration, and then the solvent was removed by evaporation under reduced pressure. The resultant residue was purified by column chromatography to provide 9.8 g (0.011 mol, 67% yield) of a compound (3-2).

APCI-TOFMS, m/z 863 [M+H]+

Example 4

Synthesis of Compound (3-1)

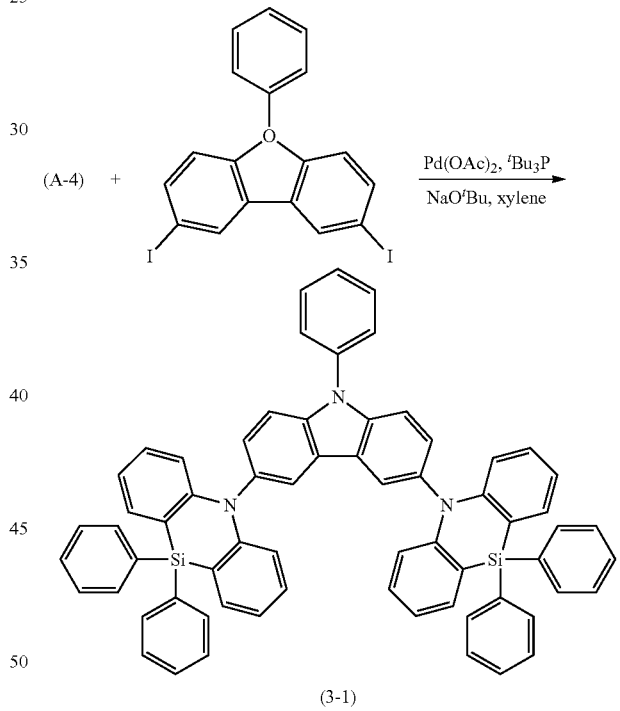

(3-1)

Under a nitrogen atmosphere, 0.07 g (0.00031 mol) of palladium acetate and 10 ml of xylene were loaded and the mixture was stirred at room temperature. 0.24 g (0.0012 mol) of t-butylphosphine was added thereto and the mixture was stirred at 80° C. for 1 hr. Separately, under a nitrogen atmosphere, 10.8 g (0.031 mol) of the intermediate (A-4), 7.33 g (0.015 mol) of 3,6-diiodo-9-phenylcarbazole, 5.96 g (0.062 mol) of sodium-t-butoxide, and 100 ml of xylene were loaded and the mixture was stirred at 80° C. The previously prepared solution was added thereto, and the mixture was stirred at 145° C. for 2 hr. Subsequently, reaction solution was cooled to room temperature, an inorganic salt was separated by filtration, and then the solvent was removed by evaporation under reduced pressure. The resultant residue was purified by column chromatography to provide 9.1 g (0.0097 mol, 65% yield) of a compound (3-1).

APCI-TOFMS, m/z 938 [M+H]$^+$

Example 5

Synthesis of Compound (1-2)

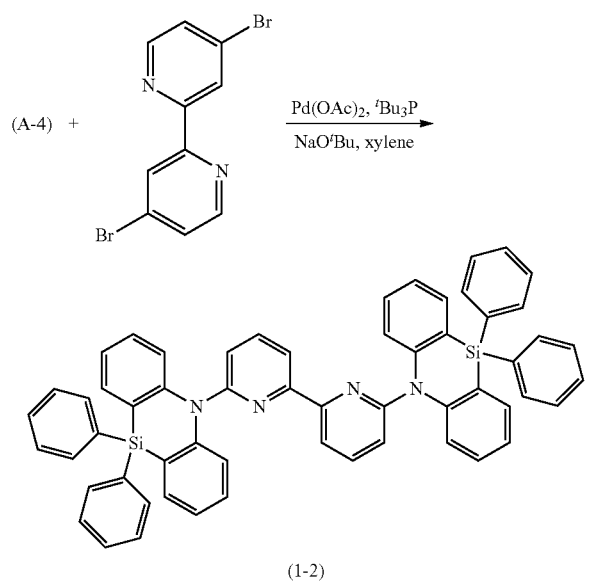

(1-2)

Under a nitrogen atmosphere, 0.05 g (0.00023 mol) of palladium acetate and 8 ml of xylene were loaded and the mixture was stirred at room temperature. 0.19 g (0.00092 mol) of t-butylphosphine was added thereto and the mixture was stirred at 80° C. for 1 hr. Separately, under a nitrogen atmosphere, 8.0 g (0.023 mol) of the intermediate (A-4), 3.45 g (0.011 mol) of 6,6'-dibromo-2,2'-bipyridine, 4.4 g (0.046 mol) of sodium-t-butoxide, and 80 ml of xylene were loaded and the mixture was stirred at 80° C. The previously prepared solution was added thereto, and the mixture was stirred at 145° C. for 2 hr. Subsequently, the reaction solution was cooled to room temperature, an inorganic salt was separated by filtration, and then the solvent was removed by evaporation under reduced pressure. The resultant residue was purified by column chromatography to provide 5.8 g (0.007 mol, 62% yield) of a compound (1-2).

APCI-TOFMS, m/z 851 [M+H]$^+$

Example 6

Synthesis of Compound (3-10)

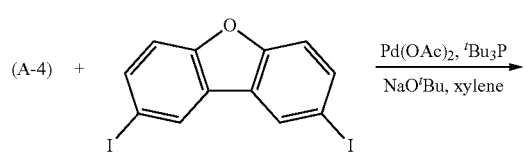

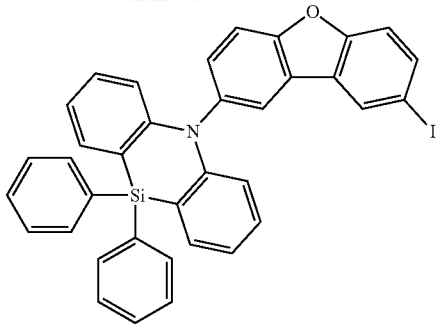

(B-1)

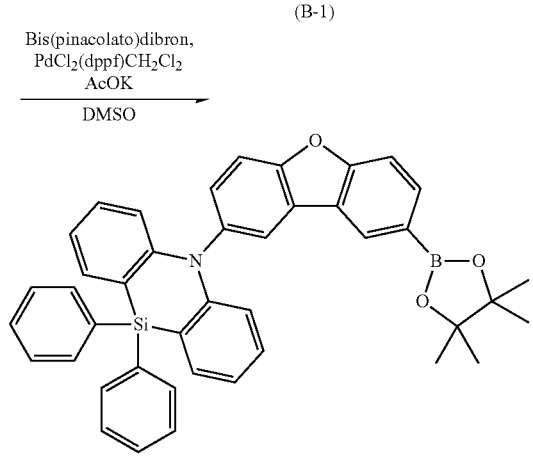

(B-2)

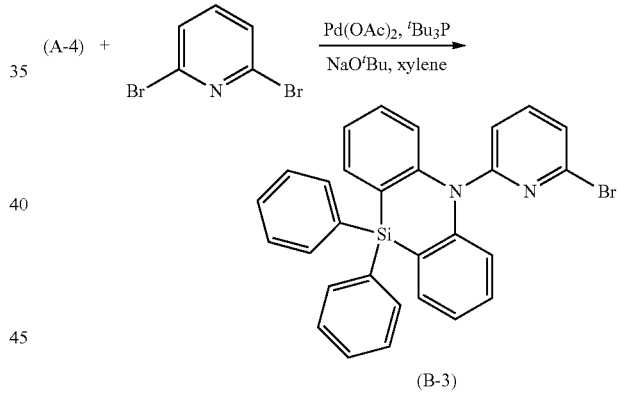

(B-3)

Under a nitrogen atmosphere, 0.04 g (0.00018 mol) of palladium acetate and 5 ml of xylene were loaded and the mixture was stirred at room temperature. 0.15 g (0.0007 mol) of t-butylphosphine was added thereto and the mixture was stirred at 80° C. for 1 hr. Separately, under a nitrogen atmosphere, 6.3 g (0.018 mol) of the intermediate (A-4), 7.11 g (0.017 mol) of 2,8-diiododibenzofuran, 3.47 g (0.036 mol) of sodium-t-butoxide, and 100 ml of xylene were loaded and the mixture was stirred at 80° C. The previously prepared solution was added thereto, and the mixture was stirred at 145° C. for 2 hr. Subsequently, the reaction solution was cooled to room temperature, an inorganic salt was separated by filtration, and then the solvent was removed by evaporation under reduced pressure. The resultant residue was purified by column chromatography to provide 4.6 g (0.007 mol, 42% yield) of an intermediate (B-1).

Under a nitrogen atmosphere, 7.0 g (0.011 mol) of the intermediate (B-1), 5.5 g (0.022 mol) of bispinacolatodiboron, 1.8 g (0.0022 mol) of a 1,1'-bis(diphenylphosphino) ferrocene-palladium(II)dichloride-dichloromethane complex, 8.6 g (0.088 mol) of potassium acetate, and 200 ml of DMSO were loaded and the mixture was stirred at 90° C. for 4 hr. Subsequently, the reaction solution was cooled to room temperature, an inorganic salt was separated by filtration, and then the filtrate was dropped into 1,000 ml of distilled water. The precipitated solid was separated by filtration and then dissolved in toluene, and the organic layer was washed with distilled water (2×100 ml). After that, the resultant organic layer was dried over anhydrous magnesium sulfate, and then the solvent was removed by evaporation under reduced pressure. The resultant residue was purified by column chromatography to provide 3.5 g (0.005 mol, 50% yield) of an intermediate (B-2).

Under a nitrogen atmosphere, 0.03 g (0.00012 mol) of palladium acetate and 4 ml of xylene were loaded and the mixture was stirred at room temperature. 0.1 g (0.00046 mol) of t-butylphosphine was added thereto and the mixture was stirred at 80° C. for 1 hr. Separately, under a nitrogen atmosphere, 4.0 g (0.012 mol) of the intermediate (A-4), 1.51 g (0.011 mol) of 2,6-dibromopyridine, 2.2 g (0.023 mol) of sodium-t-butoxide, and 80 ml of xylene were loaded and the mixture was stirred at 80° C. The previously prepared solution was added thereto, and the mixture was stirred at 145° C. for 2 hr. Subsequently, the reaction solution was cooled to room temperature, an inorganic salt was separated by filtration, and then the solvent was removed by evaporation under reduced pressure. The resultant residue was purified by column chromatography to provide 2.11 g (0.004 mol, 38% yield) of an intermediate (B-3).

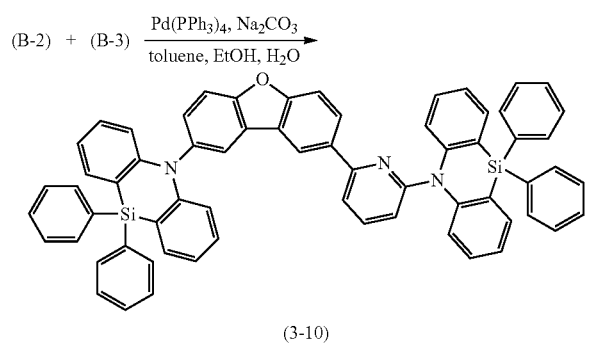

(3-10)

5.0 g (0.008 mol) of the intermediate (B-2), 3.94 g (0.008 mol) of the intermediate (B-3), 0.1 g (0.0008 mol) of tetrakis(triphenylphosphine) palladium[0], 100 ml of toluene, and 50 ml of ethanol were loaded and the mixture was stirred. To the mixture was added an aqueous solution of sodium carbonate prepared by dissolving 3.1 g (0.032 mol) of sodium carbonate in 50 ml of water, and the whole was stirred at 100° C. for 8 hr. The reaction solution was cooled to room temperature. The organic layer was washed with distilled water (2×100 ml). After that, the resultant organic layer was dried over anhydrous magnesium sulfate, and then the solvent was removed by evaporation under reduced pressure. The resultant residue was purified by column chromatography to provide 5.9 g (0.006 mol, 81% yield) of a compound (3-10) as white powder.

APCI-TOFMS, m/z 940 [M+H]$^+$

Example 7

Each thin film was laminated by a vacuum deposition method at a degree of vacuum of $2.0 \times 10^{-5}$ Pa on a glass substrate on which an anode formed of indium tin oxide (ITO) having a thickness of 110 nm had been formed. First, copper phthalocyanine (CuPC) was formed into a layer having a thickness of 25 nm to serve as a hole-injecting layer on the ITO. Next, N,N-di(naphthalen-1-yl)-N,N-diphenyl-benzidine (NPB) was formed into a layer having a thickness of 90 nm to serve as a hole-transporting layer. Next, the compound (1-25) as a host material for a light-emitting layer and an iridium complex FIrpic, a blue phosphorescent material as a dopant, were co-deposited from different deposition sources onto the hole-transporting layer to form a light-emitting layer having a thickness of 30 nm. The concentration of FIrpic was 10%. Next, Alq3 was formed into a layer having a thickness of 30 nm to serve as an electron-transporting layer. Further, lithium fluoride (LiF) was formed into a layer having a thickness of 1.0 nm to serve as an electron-injecting layer on the electron-transporting layer. Finally, aluminum (Al) was formed into a layer having a thickness of 70 nm to serve as an electrode on the electron-injecting layer. Thus, an organic EL device was produced.

An external power source was connected to the resultant organic EL device to apply a DC voltage. As a result, it was confirmed that the organic EL device had such light-emitting characteristics as shown in Table 1. A luminance, voltage, and luminous efficiency in Table 1 show values at 2.5 mA/cm$^2$. It should be noted that it was found that the local maximum wavelength of the emission spectrum of the device was 475 nm and hence light emission from FIrpic was obtained.

Examples 8 to 12

Organic EL devices were each produced in the same manner as in Example 7 except that the compound (1-1), (3-2), (3-1), (1-2), or (3-10) was used instead of the compound (1-25) as the host material for the light-emitting layer in Example 7. It was identified that the local maximum wavelength of the emission spectrum of each of the devices was 475 nm and hence light emission from FIrpic was obtained.

Comparative Example 1

An Organic EL device was produced in the same manner as in Example 1 except that mCP was used as the host material for the light-emitting layer. It was identified that the local maximum wavelength of the emission spectrum of the device was 475 nm and hence light emission from FIrpic was obtained.

Comparative Example 2

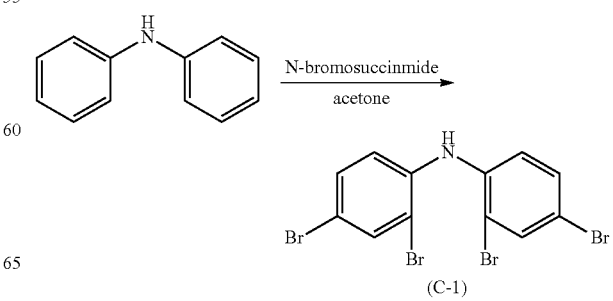

(C-1)

-continued

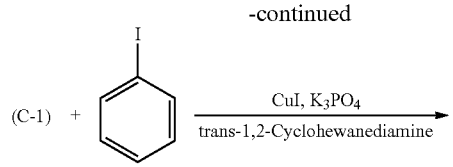

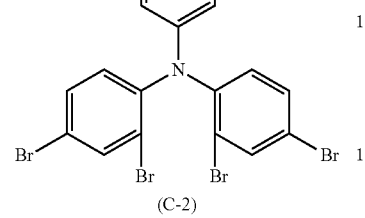

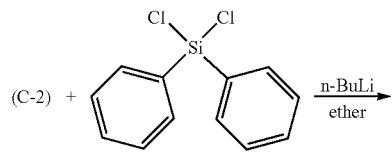

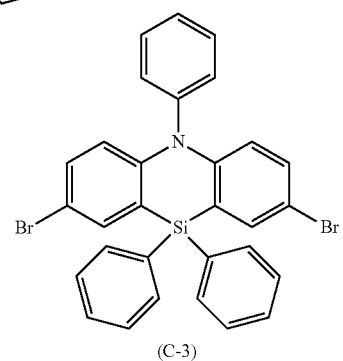

Under a nitrogen atmosphere, 15.0 g (0.089 mol) of diphenylamine, 79.2 g (0.445 mol) of N-bromosuccinimide, and 1,000 ml of acetone were loaded and the mixture was stirred at room temperature for 24 hr. After that, the solvent was removed by evaporation under reduced pressure. The resultant residue was purified by column chromatography to provide 38.8 g (0.080 mol, 90% yield) of an intermediate (C-1).

Under a nitrogen atmosphere, 20.0 g (0.041 mol) of the intermediate (C-1), 836.4 g (4.1 mol) of iodobenzene, 0.78 g (0.0041 mol) of copper (I) iodide, 34.8 g (0.16 mol) of tripotassiumphosphate, and 4.68 g (0.041 mol) of trans-1, 2-cyclohexanediamine were loaded and the mixture was stirred at 180° C. for 6 hr. Subsequently, the reaction solution was cooled to room temperature, an inorganic salt was separated by filtration, and then the solvent was removed by evaporation under reduced pressure. The resultant residue was purified by column chromatography to provide 19.6 g (0.035 mol, 85% yield) of a compound (C-2).

Under a nitrogen atmosphere, 15.0 g (0.027 mol) of the intermediate (C-2) and 300 ml of ether were loaded and the mixture was stirred. The mixture was cooled to 0° C., and 20 ml (0.054 mol) of 2.69 M n-BuLi/hex were added dropwise thereto. Stirring was continued at 0° C. for 0.5 hr, and then 6.8 g (0.027 mol) of dichlorodiphenylsilane dissolved in 100 ml of ether were added dropwise. After that, the mixture was stirred at room temperature for 2 hr. Subsequently, the solvent was removed by evaporation under reduced pressure, the residue was dissolved in ethyl acetate, and the organic layer was washed with distilled water (2×100 ml). After that, the resultant organic layer was dried over anhydrous magnesium sulfate, and then the solvent was removed by evaporation under reduced pressure. The resultant residue was purified by column chromatography to provide 8.8 g (0.015 mol, 54% yield) of an intermediate (C-3).

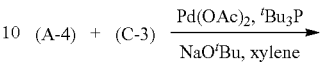

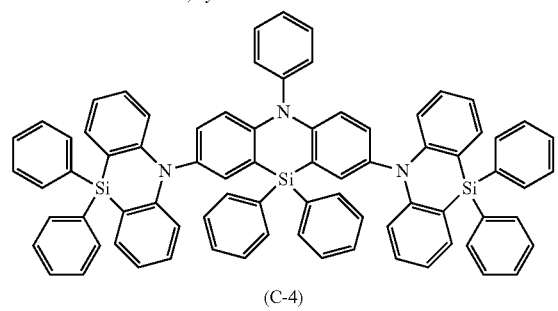

Under a nitrogen atmosphere, 0.03 g (0.00014 mol) of palladium acetate and 10 ml of xylene were loaded and the mixture was stirred at room temperature. 0.11 g (0.0006 mol) of t-butylphosphine was added thereto and the mixture was stirred at 80° C. for 1 hr. Separately, under a nitrogen atmosphere, 5.0 g (0.014 mol) of the intermediate (A-4), 4.1 g (0.015 mol) of the intermediate (C-3), 2.82 g (0.030 mol) of sodium-t-butoxide, and 100 ml of xylene were loaded and the mixture was stirred at 80° C. The previously prepared solution was added thereto, and the mixture was stirred at 145° C. for 2 hr. Subsequently, the reaction solution was cooled to room temperature, an inorganic salt was separated by filtration, and then the solvent was removed by evaporation under reduced pressure. The resultant residue was purified by column chromatography to provide 11.2 g (0.01 mol, 71% yield) of a compound (C-4).

APCI-TOFMS, m/z 1,120 [M+H]$^+$

An organic EL device was produced in the same manner as in Example 1 except that the compound (C-4) was used as the host material for the light-emitting layer. It was identified that the local maximum wavelength of the emission spectrum of the device was 475 nm and hence light emission from FIrpic was obtained.

Table 1 shows the host materials used, together with the results of the measurement of the light-emitting characteristics (at 2.5 mA/cm$^2$).

TABLE 1

| | Host Compound | Luminance (cd/m$^2$) | Voltage (V) | Visual luminous efficiency (lm/W) |
|---|---|---|---|---|
| Example 7 | 1-25 | 195 | 8.4 | 2.9 |
| 8 | 1-1 | 191 | 8.6 | 2.8 |
| 9 | 3-2 | 179 | 8.6 | 2.6 |
| 10 | 3-1 | 185 | 8.7 | 2.7 |
| 11 | 1-2 | 190 | 8.4 | 2.8 |
| 12 | 3-10 | 188 | 8.6 | 2.7 |
| Comparative Example 1 | mCP | 140 | 8.7 | 2.0 |
| 2 | C-4 | 158 | 8.8 | 2.2 |

Example 13

Each thin film was laminated by a vacuum deposition method at a degree of vacuum of $4.0 \times 10^{-5}$ Pa on a glass substrate on which an anode formed of ITO having a thickness of 110 nm had been formed. First, CuPC was formed into a layer having a thickness of 25 nm to serve as a hole-injecting layer on the ITO. Next, NPB was formed into a layer having a thickness of 40 nm to serve as a hole-transporting layer. Next, the compound (1-25) as a host material and Ir(ppy)3 as a phosphorescent light-emitting dopant were co-deposited from different deposition sources onto the hole-transporting layer to form a light-emitting layer having a thickness of 40 nm. The concentration of Ir(ppy)3 in the light-emitting layer was 10.0 wt %. Next, Alq3 was formed into a layer having a thickness of 20 nm to serve as an electron-transporting layer. Further, LiF was formed into a layer having a thickness of 1.0 nm to serve as an electron-injecting layer on the electron-transporting layer. Finally, Al was formed into a layer having a thickness of 70 nm to serve as an electrode on the electron-injecting layer. Thus, an organic EL device was produced.

An external power source was connected to the resultant organic EL device to apply a DC voltage. As a result, it was confirmed that the organic EL device had such light-emitting characteristics as shown in Table 2. A luminance, voltage, and luminous efficiency in Table 2 show values at 10 mA/cm². It should be noted that it was found that the local maximum wavelength of the emission spectrum of the device was 530 nm and hence light emission from Ir(ppy)3 was obtained.

Examples 14 to 18

Organic EL devices were each produced in the same manner as in Example 13 except that the compound (1-1), (3-2), (3-1), (1-2), or (3-10) was used instead of the compound (1-25) as the host material for the light-emitting layer in Example 13. It was identified that the local maximum wavelength of the emission spectrum of each of the devices was 530 nm and hence light emission from Ir(ppy)3 was obtained.

Comparative Examples 3 and 4

Organic EL devices were each produced in the same manner as in Example 13 except that CBP or (C-4) was used as the host material for the light-emitting layer in Example 5. It was identified that the local maximum wavelength of the emission spectrum of each of the devices was 535 nm and hence light emission from Ir(ppy)3 was obtained.

Table 2 shows the host materials used, together with the results of the measurement of the light-emitting characteristics (at 10 mA/cm²).

TABLE 2

| | Host Compound | Luminance (cd/m²) | Voltage (V) | Visual luminous efficiency (lm/W) |
|---|---|---|---|---|
| Example 13 | 1-25 | 3,250 | 7.8 | 13.1 |
| 14 | 1-1 | 3,200 | 8.1 | 12.4 |
| 15 | 3-2 | 3,180 | 8.4 | 11.9 |
| 16 | 3-1 | 3,090 | 8.6 | 11.3 |
| 17 | 1-2 | 3,210 | 8.0 | 12.6 |
| 18 | 3-10 | 3,150 | 8.3 | 11.9 |
| Comparative Example 3 | CBP | 2,420 | 9.3 | 8.2 |
| 4 | C-4 | 2,620 | 9.3 | 8.8 |

The invention claimed is:

1. An organic electroluminescent device material, comprising a compound represented by the general formula (1):

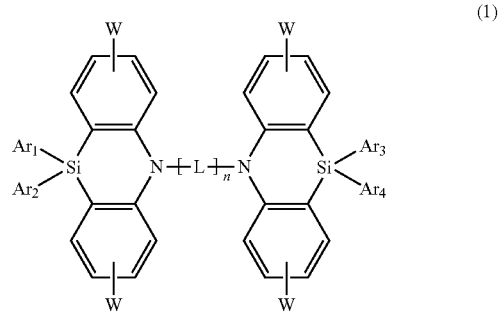

(1)

(2)

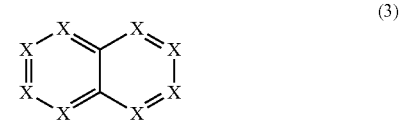

(3)

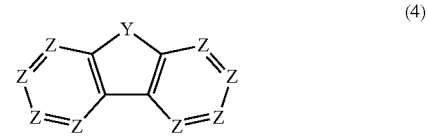

(4)

in the general formula (1):
L represents a divalent aromatic group selected from an aromatic hydrocarbon group represented by the formula (2) or (3) and having 6 to 50 carbon atoms, and an aromatic heterocyclic group represented by the formula (2), (3), or (4) and having 3 to 50 carbon atoms, and n represents an integer of from 1 to 6, provided that when n represents 1, L represents the aromatic heterocyclic group, and when n represents 2 or more, L may be different at each occurrence and at least one L represents the aromatic heterocyclic group;
in each of the formula (2) and the formula (3), X's each independently represent methine, substituted methine, a carbon atom, or nitrogen, provided that two of X's each represent a carbon atom;
in the formula (4), Y represents NR, oxygen, or sulfur, R represents an aromatic hydrocarbon group having 6 to 50 carbon atoms or an aromatic heterocyclic group having 3 to 50 carbon atoms, and Z's each independently represent methine, substituted methine, a carbon atom, or nitrogen, provided that two of Z's each represent a carbon atom;
substituents in a case where X's or Z's represent substituted methine each independently represent an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 50 carbon atoms, or an aromatic heterocyclic group having 3 to 50 carbon atoms;

W's each independently represent hydrogen, an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 50 carbon atoms, or an aromatic heterocyclic group having 3 to 50 carbon atoms; and $Ar_1$ to $Ar_4$ each independently represent an aromatic hydrocarbon group having 6 to 50 carbon atoms or an aromatic heterocyclic group having 3 to 50 carbon atoms.

2. An organic electroluminescent device material according to claim 1, wherein in the general formula (1), L represents a divalent aromatic group represented by the formula (2) or (4).

3. An organic electroluminescent device material according to claim 1, wherein:
in the general formula (1), L represents a divalent aromatic group represented by the formula (2) or (4);
at least one of X's in the formula (2) represents nitrogen; and
six of Z's in the formula (4) each represent methine and two of Z's in the formula (4) each represent a carbon atom.

4. An organic electroluminescent device material according to claim 1, wherein the compound comprises a compound represented by the general formula (5):

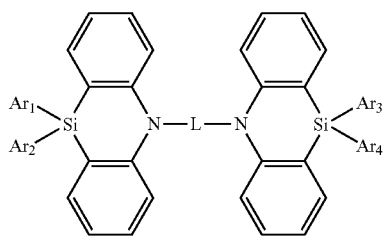

(5)

in the general formula (5), L and $Ar_1$ to $Ar_4$ have the same meanings as in the general formula (1).

5. An organic electroluminescent device material according to claim 1, wherein the compound comprises a compound represented by the general formula (6):

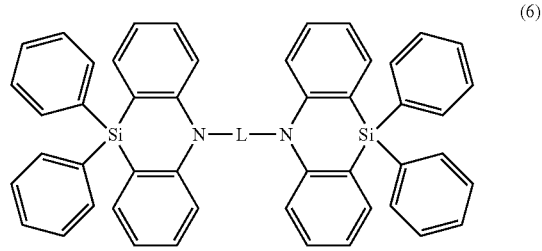

(6)

in the general formula (6), L has the same meaning as in the general formula (1).

6. An organic electroluminescent device, comprising:
a substrate;
an anode;
at least one organic layer; and
a cathode,
the anode, the at least one organic layer, and the cathode being laminated on the substrate,
wherein the at least one organic layer comprises an organic layer containing the organic electroluminescent device material according to claim 1.

7. An organic electroluminescent device according to claim 6, wherein the organic layer containing the organic electroluminescent device material comprises at least one layer selected from the group consisting of a light-emitting layer, an electron-transporting layer, a hole-transporting layer, an electron-blocking layer, and a hole-blocking layer.

8. An organic electroluminescent device according to claim 7, wherein the organic layer containing the organic electroluminescent device material is a light-emitting layer containing a phosphorescent light-emitting dopant.

9. An organic electroluminescent device, comprising:
a substrate;
an anode;
at least one organic layer; and
a cathode,
the anode, the at least one organic layer, and the cathode being laminated on the substrate,
wherein the at least one organic layer comprises an organic layer containing the organic electroluminescent device material according to claim 4.

* * * * *